US012226173B2

(12) United States Patent
Bowling et al.

(10) Patent No.: US 12,226,173 B2
(45) Date of Patent: Feb. 18, 2025

(54) SYSTEMS AND TOOLS FOR POSITIONING WORKPIECES WITH SURGICAL ROBOTS

(71) Applicant: MAKO Surgical Corp., Weston, FL (US)

(72) Inventors: David Gene Bowling, Los Ranchos de Albuquerque, NM (US); Paul Shiels, Albuquerque, NM (US); Jevin Scrivens, Weston, FL (US); Greg Starr, Albuquerque, NM (US)

(73) Assignee: MAKO Surgical Corp., Weston, FL (US)

( * ) Notice: Subject to any disclaimer, the term of this patent is extended or adjusted under 35 U.S.C. 154(b) by 462 days.

(21) Appl. No.: 17/509,369

(22) Filed: Oct. 25, 2021

(65) Prior Publication Data

US 2022/0039888 A1 Feb. 10, 2022

Related U.S. Application Data

(63) Continuation of application No. 16/003,685, filed on Jun. 8, 2018, now Pat. No. 11,185,377.

(Continued)

(51) Int. Cl.
*A61B 34/30* (2016.01)
*A61B 17/92* (2006.01)
(Continued)

(52) U.S. Cl.
CPC .............. *A61B 34/30* (2016.02); *A61B 17/92* (2013.01); *A61B 34/20* (2016.02); *A61F 2/4609* (2013.01);
(Continued)

(58) Field of Classification Search
CPC ...... B25J 17/0208; A61B 34/30; A61B 34/32; A61B 2017/0046; A61B 2017/922;
(Continued)

(56) References Cited

U.S. PATENT DOCUMENTS 4,098,001 A 7/1978 Watson
6,206,890 B1 3/2001 Truwit
(Continued)

FOREIGN PATENT DOCUMENTS

WO 2011109041 A1 9/2011
WO 2014147529 A1 9/2014

OTHER PUBLICATIONS

Partial International Search Report for Application No. PCT/US2018/036667 dated Sep. 27, 2018, 3 pages.
(Continued)

*Primary Examiner* — David W Bates
(74) *Attorney, Agent, or Firm* — Howard & Howard Attorneys PLLC

(57) ABSTRACT

Tools, assemblies, surgical systems enable impacting a prosthesis into a surgical site. The tool has an impactor head with a surface to receive an impact force that is manually imparted by a user. A tool shaft has a distal portion and a proximal portion fixed to the impactor head. The tool shaft can be supported by a robotically manipulated tool guide for alignment of the tool shaft relative to the surgical site. A compliance mechanism of the tool has a proximal body coupled to the distal portion of the tool shaft and a distal body supported by the proximal body. The distal body is adapted to releasably attach directly to the prosthesis. The distal body is moveable relative to the proximal body for providing compliant motion of the distal body and prosthesis relative to the tool shaft in response to the impact force that is manually imparted by the user.

14 Claims, 28 Drawing Sheets

Related U.S. Application Data

(60) Provisional application No. 62/517,465, filed on Jun. 9, 2017.

(51) Int. Cl.
*A61B 34/20* (2016.01)
*A61F 2/46* (2006.01)
*B25J 17/02* (2006.01)
*A61B 17/00* (2006.01)
*A61F 2/30* (2006.01)

(52) U.S. Cl.
CPC . *B25J 17/0208* (2013.01); *A61B 2017/00477* (2013.01); *A61B 2017/925* (2013.01); *A61B 2034/2055* (2016.02); *A61B 2034/305* (2016.02); *A61F 2002/30538* (2013.01); *A61F 2002/4627* (2013.01); *A61F 2002/4632* (2013.01); *A61F 2002/4681* (2013.01); *A61F 2002/4687* (2013.01)

(58) Field of Classification Search
CPC ....... A61B 17/1746; A61B 17/92; A61F 2/46; A61F 2/4609; A61F 2/4611; A61F 2002/4629
See application file for complete search history.

(56) References Cited

U.S. PATENT DOCUMENTS

| | | | |
|---|---|---|---|
| 7,037,310 | B2 | 5/2006 | Murphy |
| 7,604,667 | B2 | 10/2009 | DeSmet et al. |
| 7,621,921 | B2 | 11/2009 | Parker |
| 7,725,162 | B2 | 5/2010 | Malackowski et al. |
| 7,819,875 | B2 | 10/2010 | Chana |
| 7,931,656 | B2 | 4/2011 | Parry et al. |
| 8,010,180 | B2 | 8/2011 | Quaid et al. |
| 8,167,823 | B2 | 5/2012 | Nycz et al. |
| 8,182,491 | B2 | 5/2012 | Selover et al. |
| 8,192,453 | B2 | 6/2012 | Valla |
| 8,206,405 | B2 | 6/2012 | Beverland et al. |
| 8,675,939 | B2 | 3/2014 | Moctezuma de la Barrera |
| 8,753,346 | B2 | 6/2014 | Suarez et al. |
| 8,870,886 | B2 | 10/2014 | Burgi |
| 8,900,245 | B2 | 12/2014 | Splieth et al. |
| 8,979,859 | B2 | 3/2015 | Leparmentier et al. |
| 8,992,542 | B2 | 3/2015 | Hagag et al. |
| 9,008,757 | B2 | 4/2015 | Wu |
| 9,119,655 | B2 | 9/2015 | Bowling et al. |
| 9,155,632 | B2 | 10/2015 | Termanini |
| 9,168,154 | B2 | 10/2015 | Behzadi |
| 9,198,760 | B2 | 12/2015 | Geebelen |
| 9,220,612 | B2 | 12/2015 | Behzadi |
| 9,439,781 | B2 | 9/2016 | Gibson |
| 9,468,538 | B2 | 10/2016 | Nycz et al. |
| 9,480,580 | B2 | 11/2016 | White et al. |
| 9,526,514 | B2 | 12/2016 | Kelley et al. |
| 9,649,202 | B2 | 5/2017 | Behzadi et al. |
| 9,770,306 | B2 | 9/2017 | Hagag et al. |
| 10,172,722 | B2 | 1/2019 | Behzadi et al. |
| 10,245,160 | B2 | 4/2019 | Behzadi |
| 10,245,162 | B2 | 4/2019 | Behzadi et al. |
| 10,426,540 | B2 | 10/2019 | Behzadi |
| 10,441,244 | B2 | 10/2019 | Behzadi |
| 10,456,271 | B2 | 10/2019 | Behzadi |
| 10,463,505 | B2 | 11/2019 | Behzadi |
| 10,478,318 | B2 | 11/2019 | Behzadi et al. |
| 10,603,115 | B2 | 3/2020 | van der Walt et al. |
| 10,610,379 | B2 | 4/2020 | Behzadi |
| 10,653,533 | B2 | 5/2020 | Behzadi et al. |
| 10,849,766 | B2 | 12/2020 | Behzadi |
| 10,905,456 | B2 | 2/2021 | Behzadi |
| 11,026,809 | B2 | 6/2021 | Behzadi et al. |
| 2003/0233102 | A1 | 12/2003 | Nakamura et al. |
| 2006/0241631 | A1 | 10/2006 | Kilburn et al. |
| 2007/0055291 | A1* | 3/2007 | Birkmeyer ......... A61B 17/1671 606/130 |
| 2008/0287951 | A1 | 11/2008 | Stoneburner et al. |
| 2009/0192155 | A1 | 7/2009 | Lechot et al. |
| 2010/0249796 | A1 | 9/2010 | Nycz |
| 2010/0298834 | A1 | 11/2010 | Hildebrandt |
| 2010/0331851 | A1 | 12/2010 | Huene |
| 2011/0060339 | A1 | 3/2011 | de Wekker |
| 2012/0157887 | A1 | 6/2012 | Fanson et al. |
| 2012/0209277 | A1 | 8/2012 | Leparmentier et al. |
| 2013/0158558 | A1* | 6/2013 | Preuss ................... A61B 17/92 606/91 |
| 2014/0135791 | A1* | 5/2014 | Nikou ................. A61F 2/4609 606/130 |
| 2014/0276666 | A1 | 9/2014 | Malkowski |
| 2014/0303742 | A1 | 10/2014 | Prybyla et al. |
| 2015/0182351 | A1 | 7/2015 | Behzadi |
| 2015/0245920 | A1 | 9/2015 | Andrews |
| 2016/0120611 | A1 | 5/2016 | Lohmeier |
| 2016/0242934 | A1 | 8/2016 | van der Walt et al. |
| 2017/0000540 | A1 | 1/2017 | Li et al. |
| 2017/0196704 | A1 | 7/2017 | Behzadi et al. |
| 2018/0078201 | A1 | 3/2018 | Behzadi |
| 2018/0353248 | A1 | 12/2018 | Bowling et al. |
| 2018/0353305 | A1 | 12/2018 | Bushell et al. |
| 2019/0231446 | A1 | 8/2019 | Bowling et al. |
| 2019/0350726 | A1 | 11/2019 | Behzadi |
| 2020/0121474 | A1 | 4/2020 | Pendleton et al. |

OTHER PUBLICATIONS

Wikipedia, "Remote Center Compliance", https://en.wikipedia.org/wiki/remote_center_compliance, 2017, 1 page.

\* cited by examiner

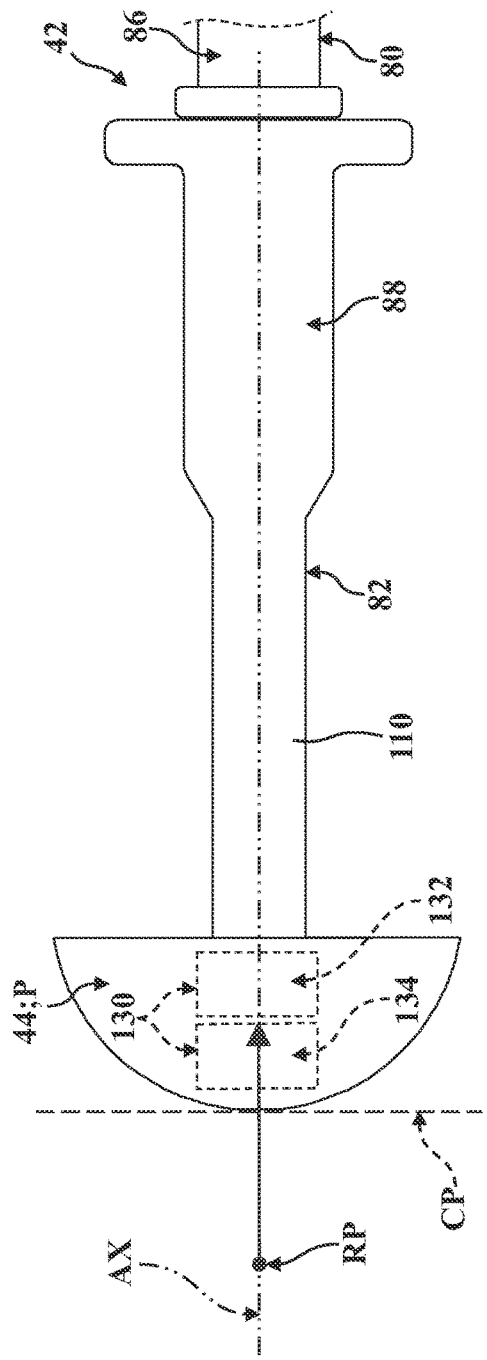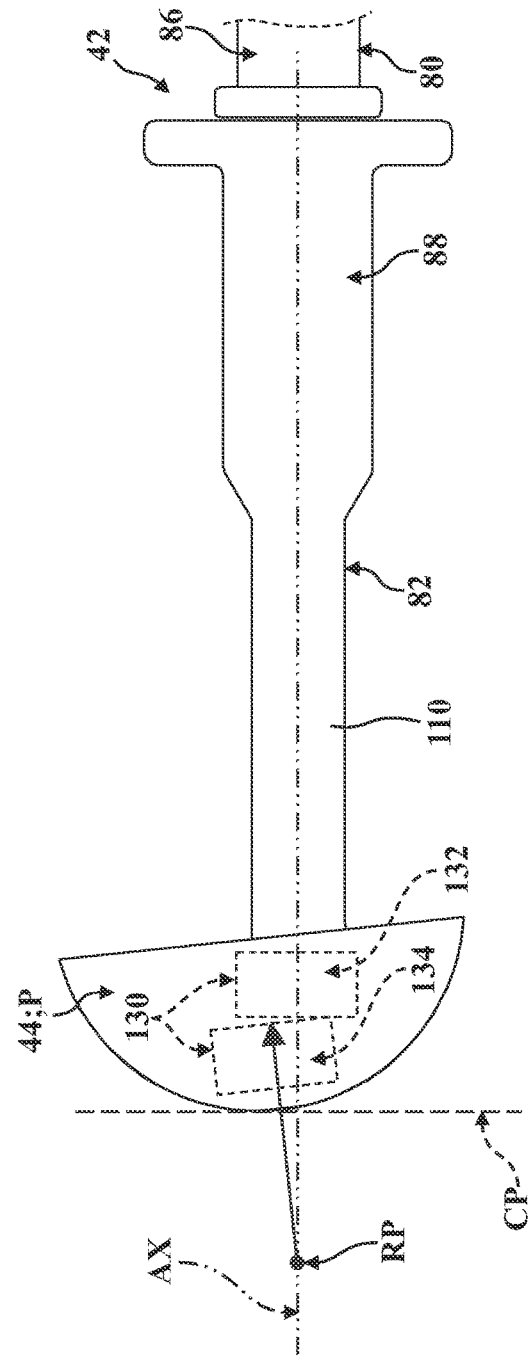

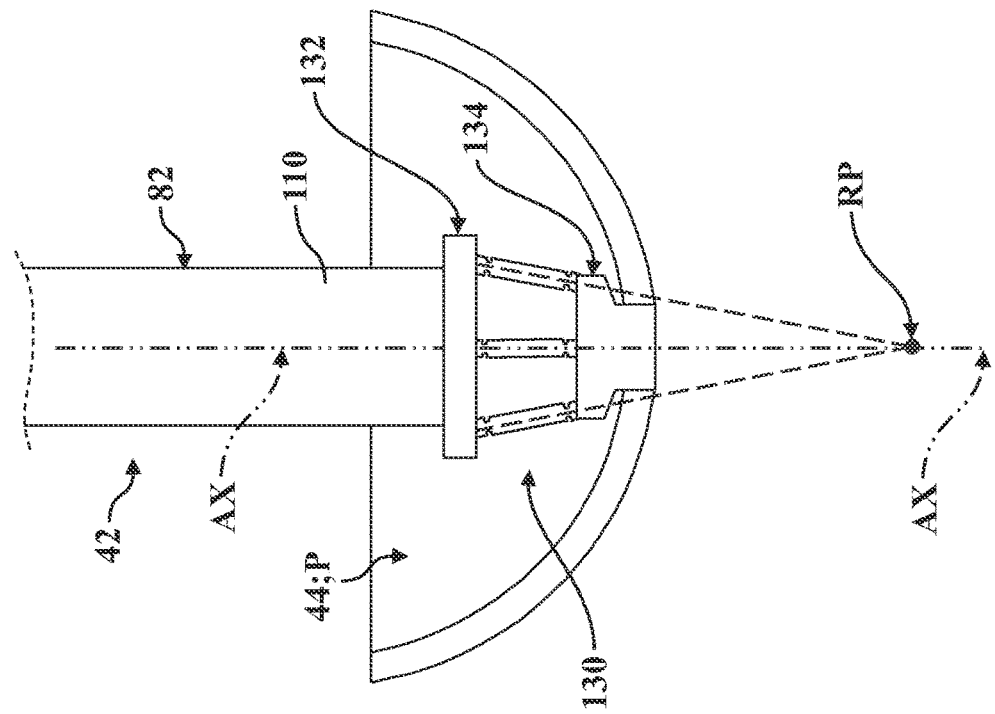
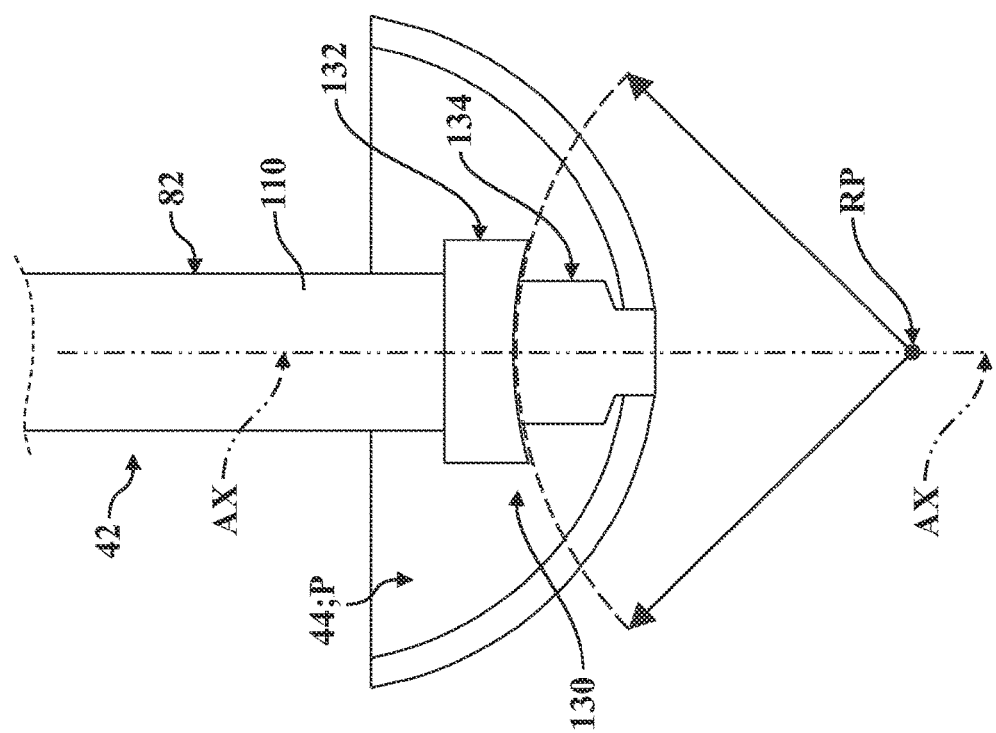

SYSTEMS AND TOOLS FOR POSITIONING WORKPIECES WITH SURGICAL ROBOTS

CROSS-REFERENCE TO RELATED APPLICATION

The subject patent application is a continuation of U.S. Nonprovisional patent application Ser. No. 16/003,685, filed Jun. 8, 2018, which claims priority to and all the benefits of U.S. Provisional Patent Application No. 62/517,465 filed on Jun. 9, 2017, the disclosures of each of the aforementioned applications being hereby incorporated by reference in their entirety.

TECHNICAL FIELD

The present disclosure relates, generally, to surgical systems and, more specifically, to systems and tools for positioning workpieces with surgical robots.

BACKGROUND

Surgical robots are frequently used to assist medical professionals in carrying out various conventional surgical procedures. To this end, a surgeon may use a surgical robot to guide, position, move, actuate, or otherwise manipulate various tools, components, prostheses, and the like during surgery.

It will be appreciated that surgical robots can be used to assist surgeons in performing a number of different types of surgical procedures. By way of illustrative example, surgical robots are commonly used in procedures involving the correction, resection, or replacement of degenerated joints to help improve patient mobility and reduce pain. In hip replacement procedures, for example, the surgeon replaces portions of the patient's hip joint with artificial prosthetic components. To this end, in total hip arthroplasty, the surgeon typically removes portions of the patient's femur to accommodate a prosthetic femoral component compromising a head, and resurfaces the acetabulum of the pelvis with a reamer to facilitate installing a prosthetic cup shaped to receive the head of the prosthetic femoral component.

It will be appreciated that the surgical robot may be used to help the surgeon approach the hip joint surgical site, remove portions of the hip joint, install the prosthetic components, and the like. For example, in order to install the prosthetic cup into the acetabulum of the pelvis, the surgeon connects the cup to an impactor tool to implant the cup into the reamed acetabulum by striking the impactor tool, such as with a mallet. Here, the surgical robot helps keep the impactor tool positioned relative to the surgical site, and the surgeon closely monitors the trajectory and depth of the cup during impaction to ensure proper alignment of the cup into the reamed acetabulum. However, depending on the configuration of the prosthetic components, impaction tools, and the surgical robot, ensuring that the cup is implanted properly can be complicated by a lack of visibility and limited access to the surgical site. Moreover, maintaining a set trajectory can be difficult with certain approaches and surgical techniques, whereby misalignment of the cup or other prosthetic components frequently results from improper alignment and/or application of impact force.

Accordingly, there remains a need in the art for addressing one or more of these deficiencies.

SUMMARY

In a first aspect, a tool is provided for impacting a prosthesis into a surgical site, the tool comprising: an impactor head comprising a surface configured to receive an impact force that is manually imparted by a user; a tool shaft including a proximal portion and a distal portion, the proximal portion of the tool shaft being fixed to the impactor head; and a compliance mechanism comprising: a proximal body coupled to the distal portion of the tool shaft; and a distal body supported by the proximal body and comprising an interface adapted to releasably attach directly to the prosthesis, wherein the distal body is moveable relative to the proximal body for providing compliant motion of the distal body relative to the tool shaft in response to the impact force that is manually imparted by the user.

In a second aspect, an assembly is provided which includes a prosthesis; and a tool comprising: an impactor head comprising a surface configured to receive an impact force that is manually imparted by a user; a tool shaft including a proximal portion and a distal portion, the proximal portion of the tool shaft being fixed to the impactor head; and a compliance mechanism comprising: a proximal body coupled to the distal portion of the tool shaft; and a distal body supported by the proximal body and comprising an interface attach directly to the prosthesis, the distal body and the prosthesis are concurrently moveable relative to the proximal body, and the distal body provides compliant motion for the prosthesis relative to the tool shaft in response to the impact force that is manually imparted by the user.

In a third aspect, a surgical system is provided which comprises: a surgical robot comprising a base, an arm coupled to the base, and a tool guide coupled to the arm; and a tool for impacting a prosthesis into a surgical site, the tool comprising: an impactor head comprising a surface configured to receive an impact force that is manually imparted by a user; a tool shaft configured to be supported by the tool guide for alignment of the tool shaft relative to the surgical site, the tool shaft including a proximal portion and a distal portion, the proximal portion of the tool shaft being fixed to the impactor head; and a compliance mechanism comprising: a proximal body coupled to the distal portion of the tool shaft; and a distal body supported by the proximal body and comprising an interface adapted to releasably attach directly to the prosthesis, wherein the distal body is moveable relative to the proximal body for providing compliant motion of the distal body relative to the tool shaft in response to the impact force that is manually imparted by the user.

Other features and advantages of the present disclosure will be readily appreciated, as the same becomes better understood, after reading the subsequent description taken in conjunction with the accompanying drawings.

BRIEF DESCRIPTION OF THE DRAWINGS

FIG. 13A is a partial schematic view of the tool and prosthesis of FIGS. 9A-9G, shown with a compliance mechanism interposed between the prosthesis and the second assembly to facilitate movement of the prosthesis about a remote point along the axis according to one embodiment.

FIG. 13B is another partial schematic view of the tool and prosthesis of FIG. 13A, shown with the prosthesis articulated about the remote point along the axis.

FIG. 15A is a schematic illustration of the prosthesis, a portion of the tool, and one embodiment of the compliance mechanism depicted in FIGS. 13A-13B.

FIG. 15B is a schematic illustration of the prosthesis, a portion of the tool, and one embodiment of the compliance mechanism depicted in FIGS. 13A-13B.

DETAILED DESCRIPTION

Figure 1A:
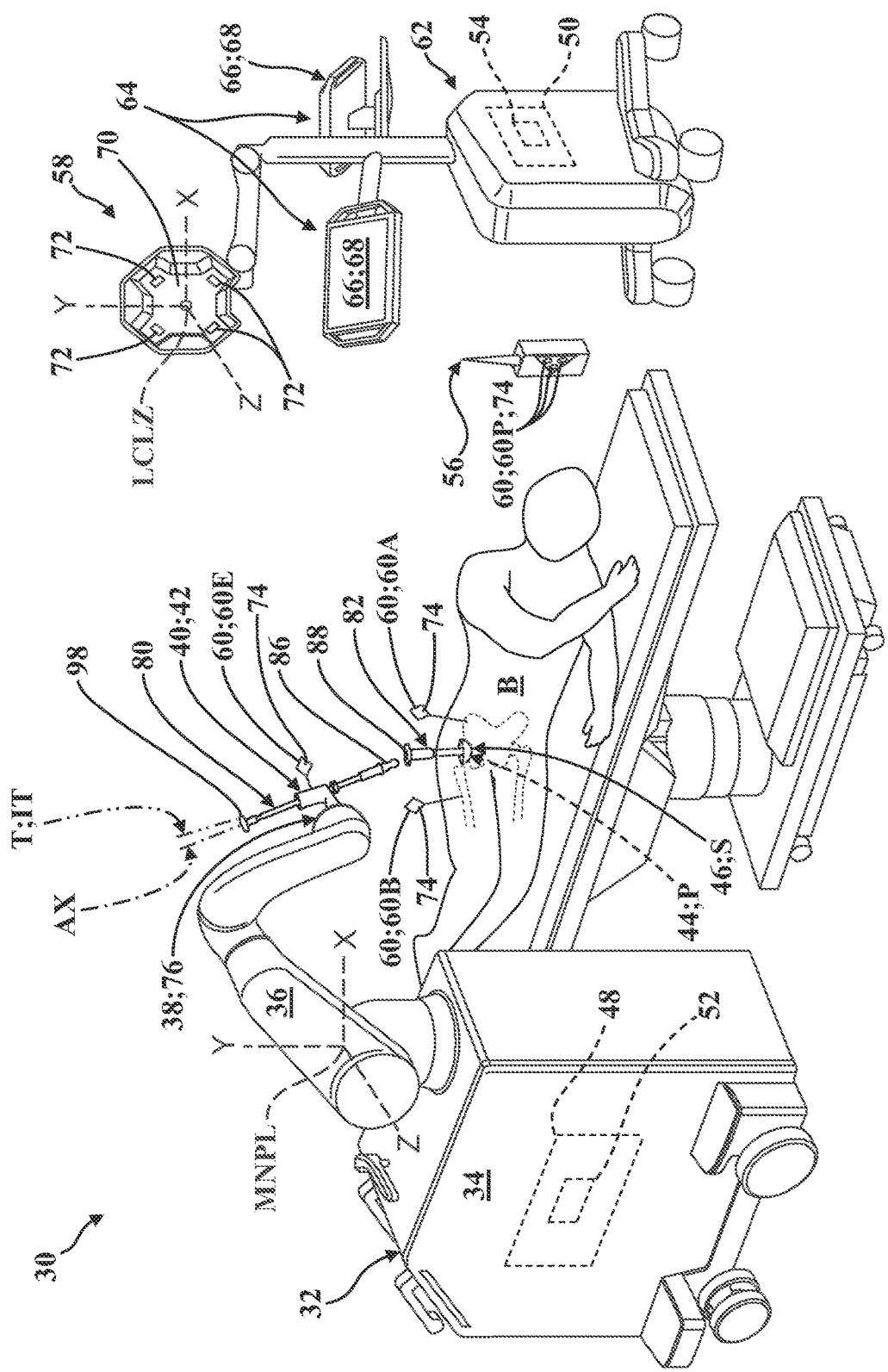
FIG. 1A is a partial perspective view of a surgical system comprising a surgical robot and a tool for installing a prosthesis according to one embodiment, with the tool shown having a first assembly coupled to the surgical robot, and having a second assembly, adapted to attach to the prosthesis, spaced from the first assembly at a surgical site.
Figure 1B:
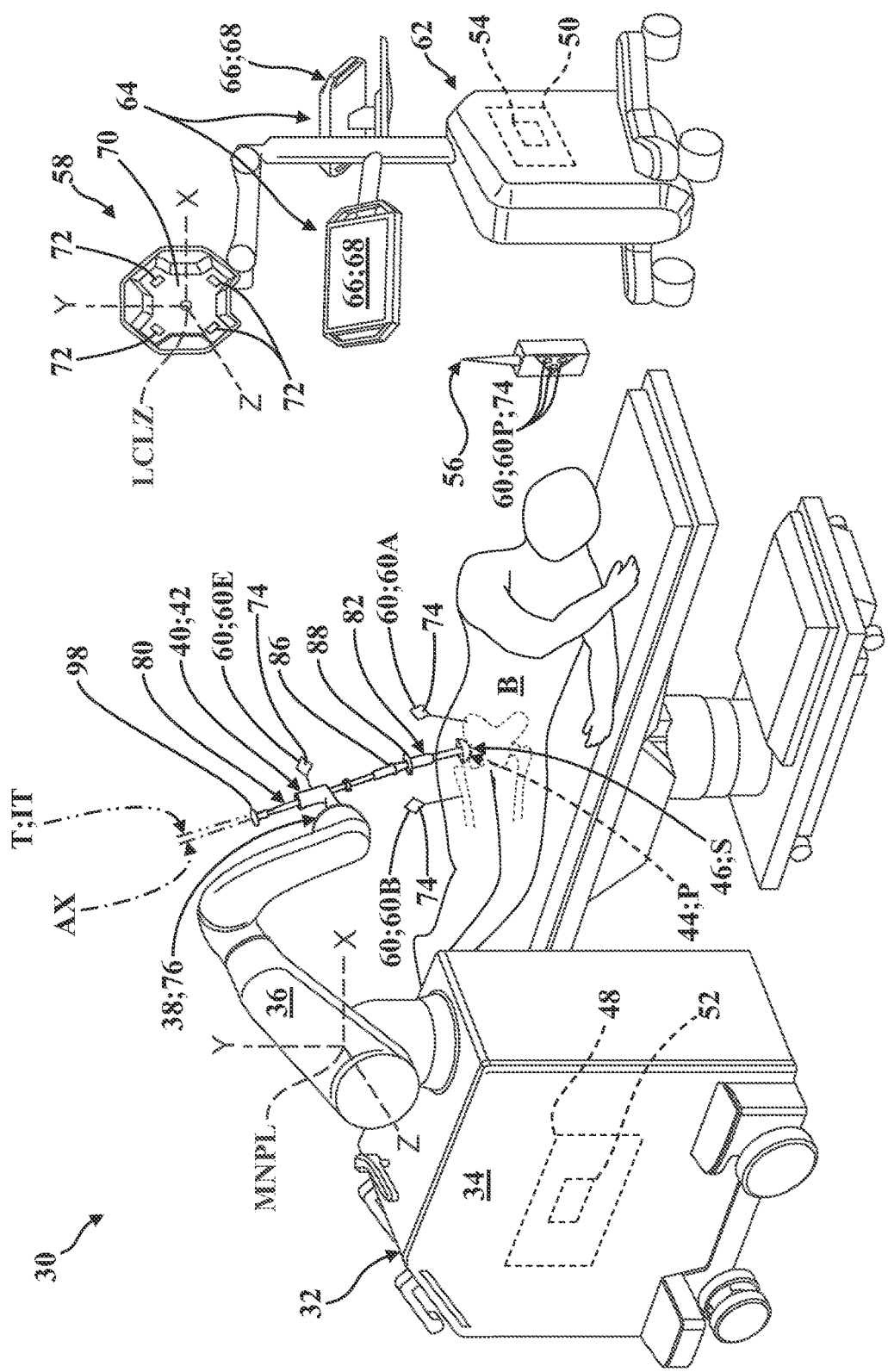
FIG. 1B is another partial perspective view of the surgical system of FIG. 1A, shown with the first and second assemblies moved into initial engagement with each other.
Figure 1C:
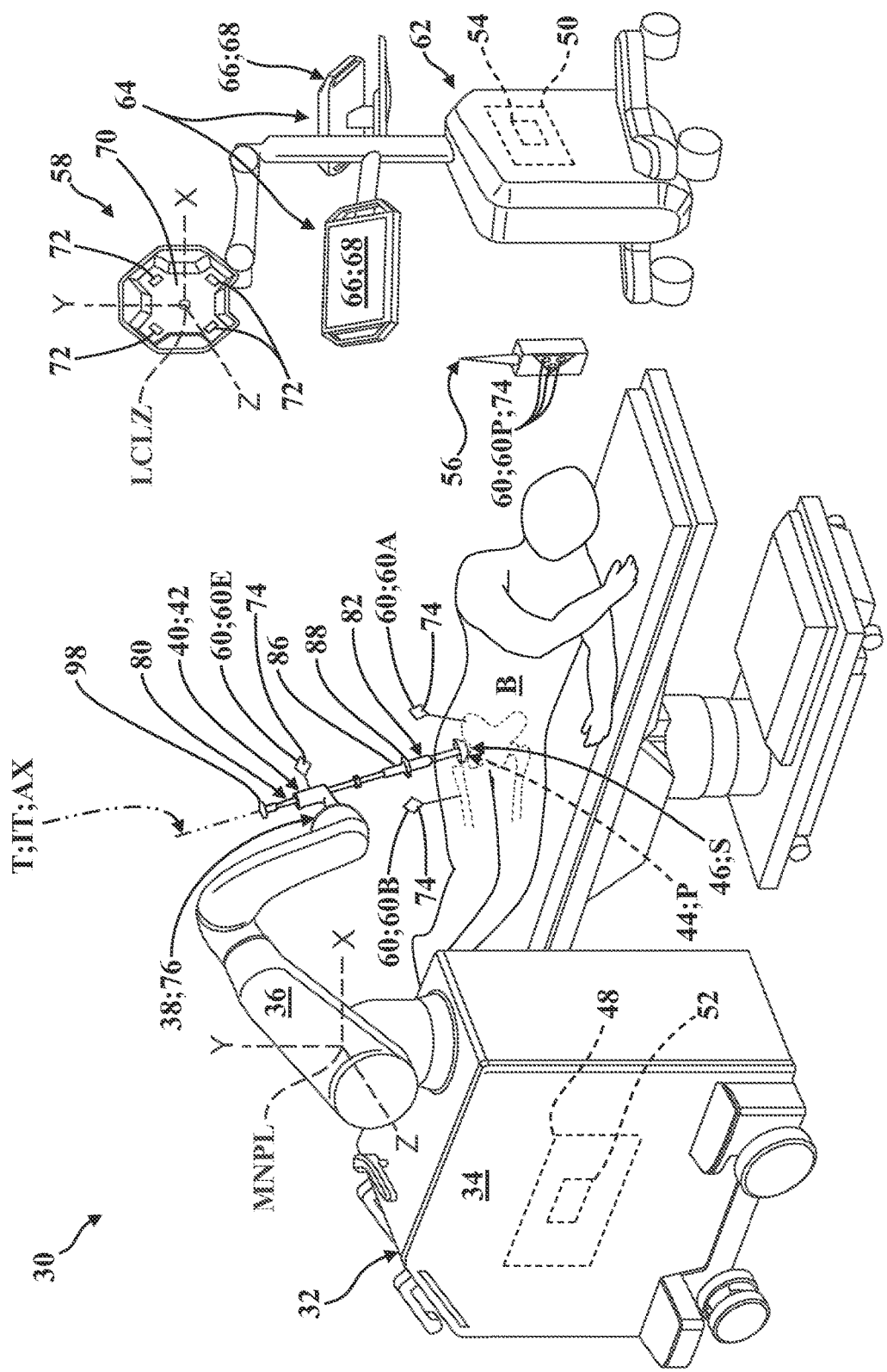
FIG. 1C is another partial perspective view of the surgical system of FIGS. 1A-1B, shown with the first and second assemblies engaging each other and aligned about an axis.
Figure 2:
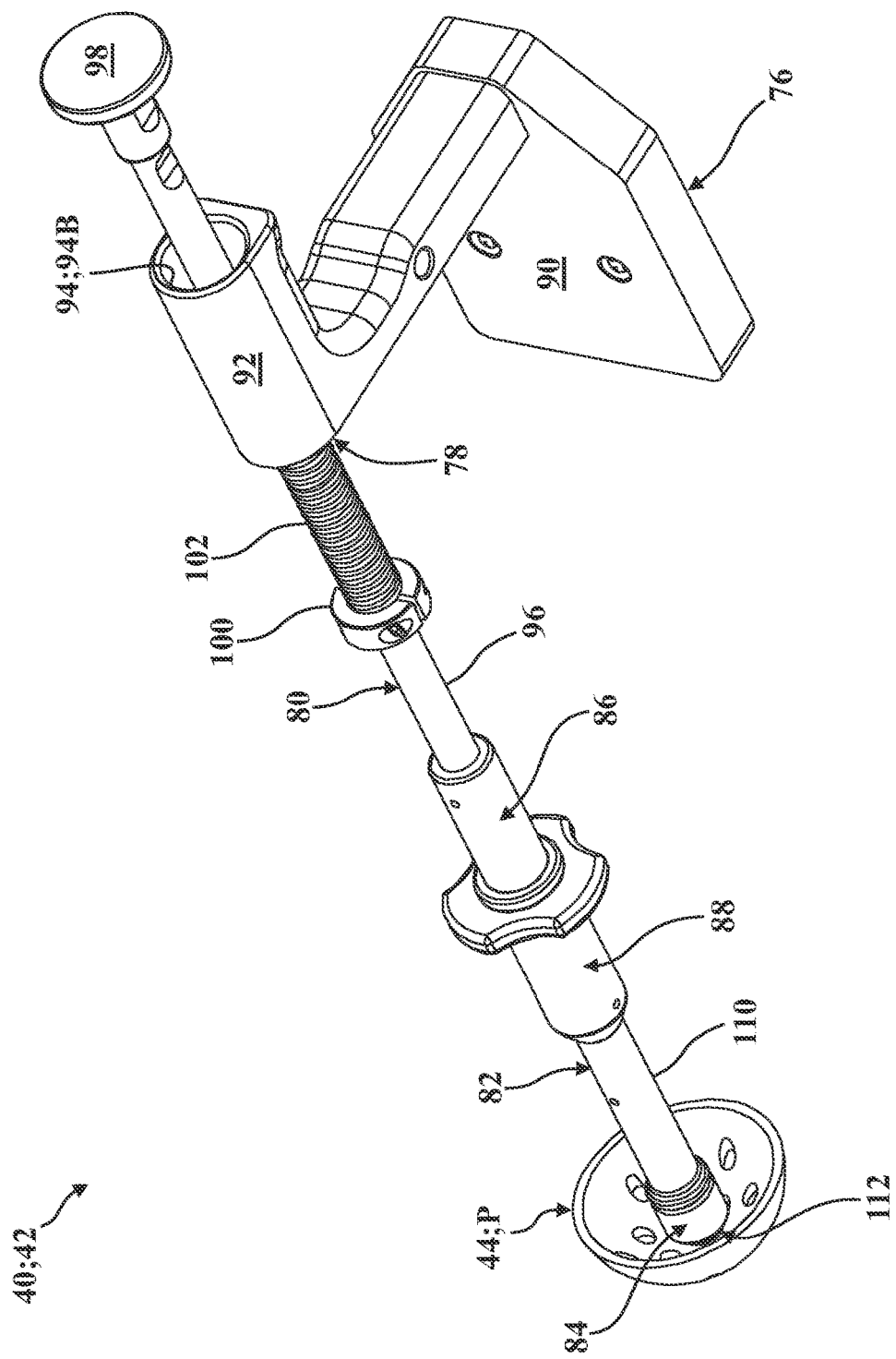
FIG. 2 is a perspective view of the tool of FIGS. 1A-1C, with the first assembly shown supported by a mount adapted to attach to the surgical robot, and with the second assembly shown attached to a prosthesis and engaged in alignment with the first assembly.
Figure 3:
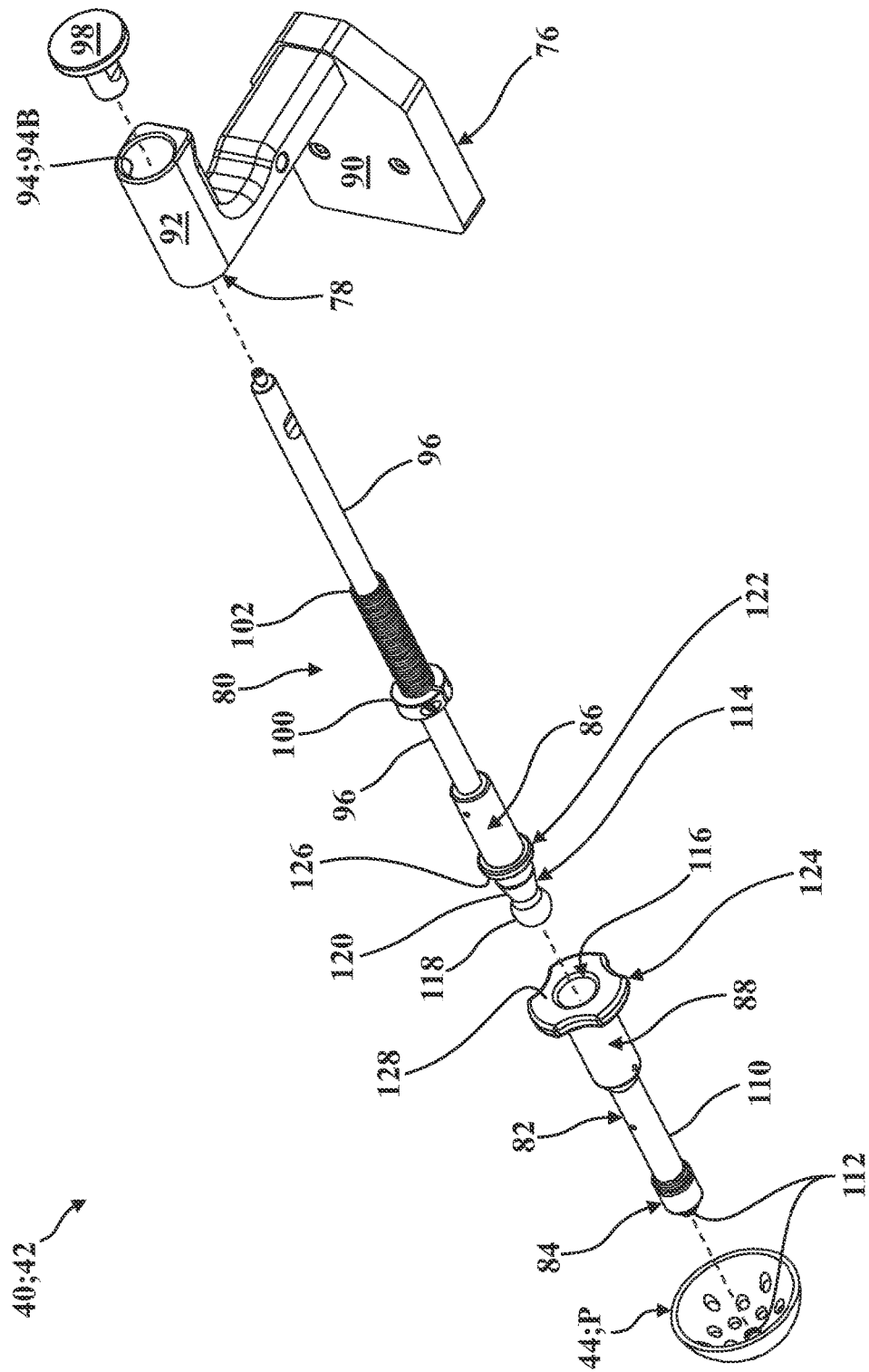
FIG. 3 is a partially-exploded perspective view of the tool and prosthesis of FIG. 2.
Figure 4:
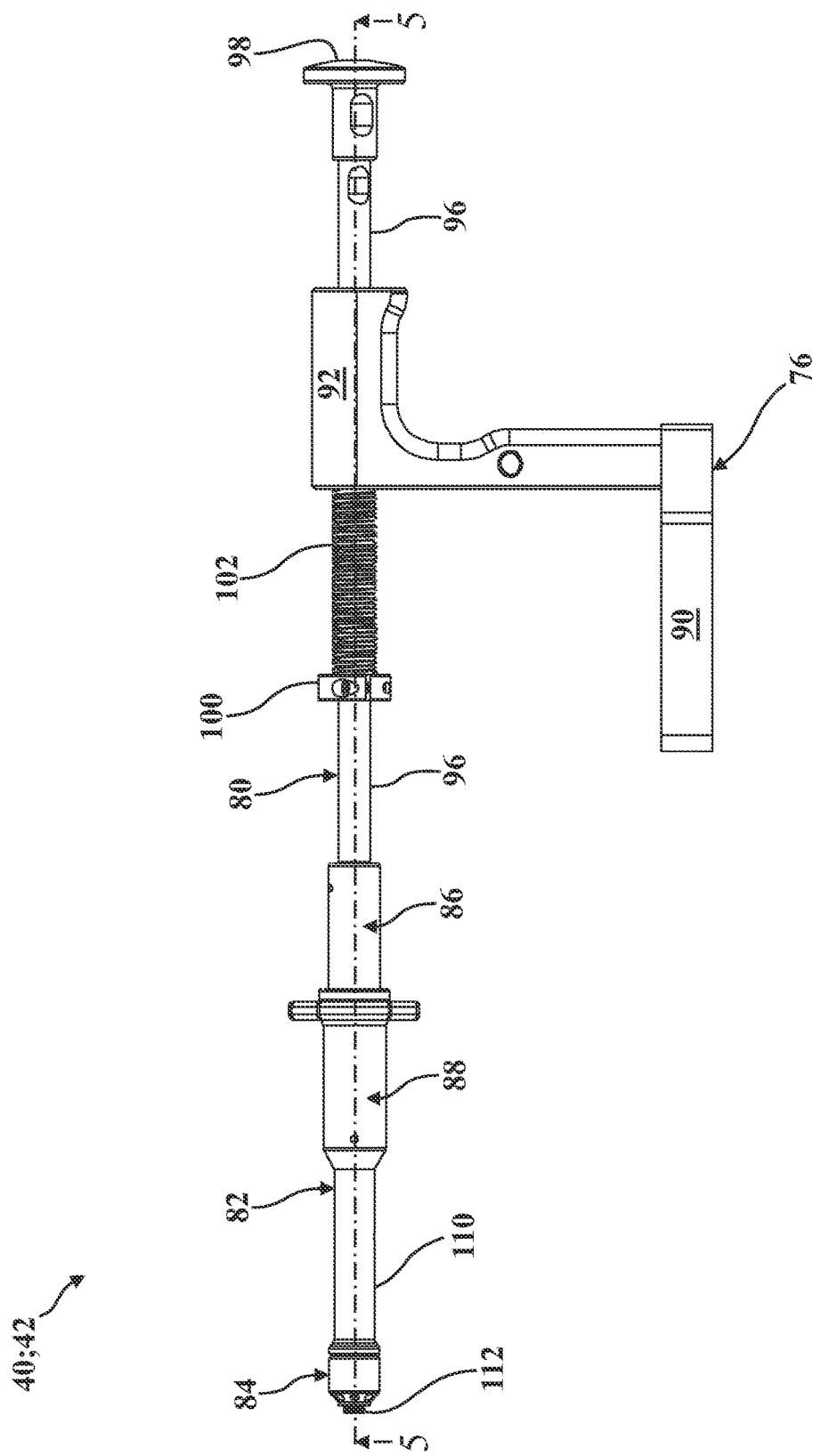
FIG. 4 is a left-side plan view of the tool of FIGS. 1A-3.

Referring now to FIGS. 1A-1C, a surgical system 30 comprising a surgical robot 32 is shown. The surgical robot 32 generally comprises a base 34, a robotic arm 36, and an end effector coupling 38. As is described in greater detail below, the robotic arm 36 is supported by the base 34 and is configured to move, drive, maintain, or otherwise adjust the position and/or orientation of the end effector coupling 38 relative to the base 34 during use. The end effector coupling 38 is adapted to releasably secure an end effector 40 which, in turn, comprises or otherwise supports a tool, generally indicated at 42. The tool 42 is configured to support, position, or otherwise facilitate driving a workpiece 44 used in connection with surgical procedures, as described in greater detail below. In some embodiments, the surgical system 30 is configured to guide the workpiece 44 to a target, generally indicated at 46 along or with respect to a trajectory T maintained by the surgical robot 32. In the representative embodiment illustrated herein, the target 46 is a surgical site S on a patient's body B, and the workpiece 44 is a prosthesis P supported by the tool 42 and adapted for implantation at the surgical site S along a trajectory T (e.g., along an impaction trajectory IT). However, as will be appreciated from the subsequent description below, the end effector 40, the tool 42, the workpiece 44, and/or the target 46 could be defined in a number of different ways without departing from the scope of the present disclosure. By way of non-limiting example, the tool could be a rotary surgical instrument which drives a workpiece realized as a drill bit or reamer head guided by the surgical robot 32. Other configurations are contemplated.

The surgical robot 32 moves the end effector 40, relative to the target 46 via the robotic arm 36 to, among other things, assist medical professionals in carrying out various types of surgical procedures with precise control over movement and positioning of the tool 42 and/or the workpiece 44. One exemplary arrangement of the robotic arm 36 is described in U.S. Pat. No. 9,119,655, entitled, "Surgical Robotic arm Capable of Controlling a Surgical Instrument in Multiple Modes," the disclosure of which is hereby incorporated by reference in its entirety. Another exemplary arrangement of the robotic arm 36 is described in U.S. Pat. No. 8,010,180, entitled, "Haptic Guidance System and Method," the disclosure of which is hereby incorporated by reference in its entirety. It will be appreciated that the robotic arm 36 and other portions of the surgical robot 32 may be arranged in alternative configurations.

The surgical system 30 is able to monitor, track, and/or determine changes in the relative position and/or orientation of one or more parts of the surgical robot 32, the robotic arm 36, the end effector 40, the tool 42, and/or the workpiece 44, as well as various parts of the patient's body B, within a common coordinate system by utilizing various types of trackers (e.g., multiple degree-of-freedom optical, inertial, and/or ultrasonic sensing devices), navigation systems (e.g., machine vision systems, charge coupled device cameras, tracker sensors, surface scanners, and/or range finders), anatomical computer models (e.g., magnetic resonance imaging scans of the patient's anatomy), data from previous surgical procedures and/or previously-performed surgical techniques (e.g., data recorded while reaming the acetabulum that are subsequently used to facilitate impacting the prosthesis), and the like. To these ends, and as is depicted schematically in FIGS. 1A-1C, the surgical system 30 generally comprises a robotic control system 48 and a navigation system 50 which cooperate to allow the surgical robot 32 maintain alignment of the end effector 40 relative to the trajectory T.

As is depicted schematically in FIGS. 1A-1C, the robotic control system 48 comprises a robot controller 52, and the navigation system 50 comprises a navigation controller 54. In the illustrated embodiment, the robot controller 52 and the navigation controller 54 are disposed in communication with each other and/or with other components of the surgical system 30 such as via physical electrical connections (e.g., a tethered wire harness) and/or via one or more types of wireless communication (e.g., with a WiFi™ network, Bluetooth®, a radio network, and the like). The robot controller 52 and/or the navigation controller 54 may be realized as computers, processors, control units, and the like, and may be discrete components, may be integrated, and/or may otherwise share hardware, software, inputs, outputs, and the like.

The surgical system 30 employs the robotic control system 48 to, among other things, articulate the robotic arm 36, maintain the trajectory T, and the like. Here, the robot controller 52 of the robotic control system 48 is configured to articulate the robotic arm 36 by driving various actuators, motors, and the like disposed at joints of the robotic arm 36 (not shown). The robot controller 52 also gathers data from various sensors such as encoders located along the robotic arm 36 (not shown). Because the specific geometry of each of the components of the surgical robot 32 and the end effector 40 are known, these sensor data can be used by the robot controller 52 to reliably adjust the position and/or orientation of the end effector 40 and the tool 42 within a manipulator coordinate system MNPL. The manipulator coordinate system MNPL has an origin, and the origin is located relative to the robotic arm 36. One example of this type of manipulator coordinate system MNPL is described in U.S. Pat. No. 9,119,655, entitled, "Surgical Robotic Arm Capable of Controlling a Surgical Instrument in Multiple Modes," previously referenced.

The surgical system 30 employs the navigation system 50 to, among other things, track movement of various objects such as the end effector 40, a pointer 56, and parts of the patient's body B (e.g. bones or other anatomy at the surgical site S). To this end, the navigation system 50 employs a localizer 58 configured to sense the position and/or orientation of trackers 60 fixed to objects within a localizer coordinate system LCLZ. The navigation controller 54 is disposed in communication with the localizer 58 and gathers position and/or orientation data for each tracker 60 sensed within a field of view of the localizer 58 in the localizer coordinate system LCLZ.

It will be appreciated that the localizer 58 can sense the position and/or orientation of multiple trackers 60 to track correspondingly multiple objects within the localizer coordinate system LCLZ. By way of example, and as is depicted in FIGS. 1A-1C, trackers 60 may comprise a pointer tracker 60P coupled to the pointer 56, an end effector tracker 60E coupled to the end effector 40, a first patient tracker 60A, and/or a second patient tracker 60B, as well as additional patient trackers, trackers for additional medical and/or surgical tools, and the like. In the illustrated embodiment, the end effector tracker 60E is firmly affixed to the end effector 40, the first patient tracker 60A is firmly affixed to one bone of the patient's body B at the surgical site S (e.g., to the pelvis adjacent to the acetabulum), and the second patient tracker 60B is firmly affixed to a different bone (e.g., to a portion of the femur). The end effector tracker 60E could be fixed to the end effector 40 in different ways, such as by integration into the end effector 40 during manufacture or by releasable attachment to the end effector 40. The patient trackers 60A, 60B are firmly affixed to different bones in the patient's body B, such as by threaded engagement, clamping, or by other techniques. It will be appreciated that various trackers 60 may be firmly affixed to different types of tracked objects (e.g., discrete bones, tools, pointers, and the like) in a number of different ways.

The position of the trackers 60 relative to the anatomy to which they are attached can be determined by known registration techniques, such as point-based registration in which a distal tip of the pointer 56 is used to touch off on bony landmarks on bone or to touch off on several points across the bone for surface-based registration as the localizer 58 monitors the position and orientation of the pointer tracker 60P. Conventional registration techniques can then be employed to correlate the pose of the patient trackers 60A, 60B to the patient's anatomy (e.g., to each of the femur and acetabulum). Other types of registration are also possible, such as by using patient trackers 60A, 60B with mechanical clamps that attach to bone and have tactile sensors (not shown) to determine a shape of the bone to which the clamp is attached. The shape of the bone can then be matched to a 3D model of bone for registration. A known relationship between the tactile sensors and the three or more markers on the patient tracker 60A, 60B may be entered into or otherwise known by the navigation controller 54. Based on this known relationship, the positions of the markers relative to the patient's anatomy can be determined.

Position and/or orientation data may be gathered, determined, or otherwise handled by the navigation controller 54 using conventional registration/navigation techniques to determine coordinates of each tracker 60 within the localizer coordinate system LCLZ. These coordinates are communicated to the robotic control system 48 to facilitate articulation of the robotic arm 36 and/or to otherwise assist the surgeon in performing the surgical procedure, as described in greater detail below.

In the representative embodiment illustrated herein, the robot controller 52 is operatively attached to the surgical robot 32, and the navigation controller 54 and the localizer 58 are supported on a mobile cart 62 which is movable relative to the base 34 of the surgical robot 32. The mobile cart 62 also supports a user interface, generally indicated at 64, to facilitate operation of the surgical system 30 by displaying information to, and/or by receiving information from, the surgeon or another user. The user interface 64 is disposed in communication with the navigation system 50 and/or the robotic control system 48, and may comprise one or more output devices 66 (e.g., monitors, indicators, display screens, and the like) to present information to the surgeon (e.g., images, video, data, a graphics, navigable menus, and the like), and one or more input devices 68 (e.g., buttons, touch screens, keyboards, mice, gesture or voice-based input devices, and the like). One type of mobile cart 62 and user interface 64 utilized in this type of navigation system 50 is described in U.S. Pat. No. 7,725,162, entitled "Surgery System," the disclosure of which is hereby incorporated by reference in its entirety.

Because the mobile cart 62 and the base 34 of the surgical robot 32 can be positioned relative to each other and also relative to the patient's body B, the surgical system 30 transforms the coordinates of each tracker 60 sensed via the localizer 58 from the localizer coordinate system LCLZ into the manipulator coordinate system MNPL, or vice versa, so that articulation of the robotic arm 36 can be performed based at least partially on the relative positions and orientations of each tracker 60 within a single, common coordinate system (the manipulator coordinate system MNPL, the localizer coordinate system LCLZ, or another common coordinate system). It will be appreciated that coordinates within the localizer coordinate system LCLZ can be transformed into coordinates within the manipulator coordinate system MNPL, and vice versa, using a number of different conventional coordinate system transformation techniques. One example of the translation or transformation of data between coordinate systems is described in U.S. Pat. No. 8,675,939, entitled "Registration of Anatomical Data Sets", the disclosure of which is hereby incorporated by reference in its entirety.

In the illustrated embodiment, the localizer 58 is an optical localizer and includes a camera unit 70 with one or more optical position sensors 72. The navigation system 50 employs the optical position sensors 72 of the camera unit 70 to sense the position and/or orientation of the trackers 60 within the localizer coordinate system LCLZ. In the representative embodiment illustrated herein, the trackers 60 each employ markers 74 which can be sensed by the optical position sensors 72 of the camera unit 70. One example of a navigation system 50 of this type is described in U.S. Pat. No. 9,008,757, entitled, "Navigation System Including Optical and Non-Optical Sensors," the disclosure of which is hereby incorporated by reference in its entirety. In some embodiments, the markers 74 are active markers (e.g., light emitting diodes "LEDs") which emit light that is sensed by the optical position sensors 72. In other embodiments, the markers 74 may be passive markers (e.g., reflectors) which reflect light emitted from the camera unit 70 or another light source. It should be appreciated that other suitable tracking systems and methods not specifically described herein may be utilized (e.g., ultrasonic, electromagnetic, radio frequency, and the like).

In some embodiments, the surgical system 30 is capable of displaying a virtual representation of the relative positions and orientations of tracked objects to the surgeon or other users of the surgical system 30, such as with images and/or graphical representations of the anatomy of the patient's body B, the end effector 40, and/or the tool 42 presented on one or more output devices 66. The robot controller 52 and/or the navigation controller 54 may also utilize the user interface 64 to display instructions or request information such that the surgeon or other users may interact with the robotic control system 48 to facilitate articulation of the robotic arm 36. Other configurations are contemplated.

It will be appreciated that the robotic control system 48 and the navigation system 50 can cooperate to facilitate control over the position and/or orientation of the end effector 40 and/or tool 42 in different ways. By way of example, in some embodiments, the robot controller 52 is configured to control the robotic arm 36 (e.g., by driving joint motors) to provide haptic feedback to the surgeon via the robotic arm 36. Here, haptic feedback helps constrain or inhibit the surgeon from manually moving the end effector 40 and/or tool 42 beyond predefined virtual boundaries associated with the surgical procedure (e.g., to maintain alignment of the tool 42 along or with respect to the trajectory T). One type of haptic feedback system and associated haptic objects that define virtual boundaries are described, for example, in U.S. Pat. No. 8,010,180, entitled, "Haptic Guidance System and Method," the disclosure of which is hereby incorporated by reference in its entirety. In one embodiment, the surgical system 30 is the RIO™ Robotic Arm Interactive Orthopedic System manufactured by MAKO Surgical Corp. of Fort Lauderdale, FL., USA.

As noted above, in the representative embodiment illustrated in FIGS. 1A-1C, the tool 42 is provided for positioning the workpiece 44 with the surgical robot 32, where the workpiece 44 is realized as a prosthesis P adapted for implantation into the patient's body B. More specifically, the prosthesis P is a generally hemispherical-shaped cup which forms part of an artificial hip joint adapted for impaction into the patient's acetabulum, as is described in greater detail below in connection with FIGS. 9A-12C. Prior to impaction, the patient's acetabulum is reamed or otherwise prepared so as to define the target 46 at the surgical site S. The Applicant has described the reaming, preparing, and impaction processes in greater detail in U.S. Pat. Nos. 8,979,859 and 8,753,346, the disclosures of which are hereby incorporated by reference in their entirety. While the present disclosure describes various orthopedic procedures involving hip joints, it will be appreciated that the subject matter described herein may be applicable to other joints in the patient's body B, such as, for example, shoulders, elbows, wrists, spines, knees, ankles, and the like. Furthermore, while the Referring now to FIGS. 1A-9G, in one embodiment, the tool 42 of the end effector 40 comprises a mount 76, a pivot bearing 78, a first assembly 80 extending along an axis AX, and a second assembly 82 comprising an interface 84 adapted to attach to the workpiece 44. The mount 76 is adapted to attach the end effector 40 to the end effector coupling 38 of the surgical robot 32 for concurrent movement such that the robotic arm 36 can adjust the position and/or orientation of the tool 42. The pivot bearing 78 is coupled to the mount 76 and supports the first assembly 80 for rotation about and translation along the axis AX and for at least partial articulation relative to the mount 76 (compare orientation of axis AX relative to trajectory Tin FIGS. 1A-1C; see also FIGS. 9A-9G). In the representative embodiment illustrated herein, the first assembly 80 comprises a coupler 86 and the second assembly 82 comprises a receiver 88 shaped to engage the coupler 86 (see FIGS. 1A-1B) to align the second assembly 82 and the first assembly 80 along the axis AX (see FIG. 1C). While the coupler 86 is depicted as part of the first assembly 80 and the receiver 88 is depicted as part of the second assembly 82, it will be appreciated that this arrangement could be interchanged without departing from the scope of the present disclosure. As will be appreciated from the subsequent description below, in the illustrated embodiment, the first assembly 80 of the tool 42 is realized as a portion of the end effector 40 in that the first assembly 80 generally moves in response to movement of the robotic arm 36, whereas the second assembly 82 of the tool 42 is effectively "detachable" from the end effector 40 during use and under certain conditions described herein. Nevertheless, for the purposes of clarity and consistency, use of the term "tool 42" herein also generally applies to the term "end effector 40" unless specifically noted otherwise. Each of the components of the tool 42 introduced above will be described in greater detail below.

In the representative embodiment illustrated herein, and as is best depicted in FIGS. 2, 5, and 9A-9G, the mount 76 comprises a mount plate 90 which is adapted to attach to the end effector coupling 38, such as via one or more fasteners (not shown). The mount 76 is also provided with a mount body 92 that is fixed to the mount plate 90, similarly such as with one or more fasteners (not shown). The mount body 92 defines a mount aperture 94 with a distal aperture region 94A and with a proximal aperture region 94B (see FIG. 5), each of which have a generally cylindrical profile. As is described in greater detail below, the pivot bearing 78 is supported at the distal aperture region 94A, and the proximal aperture region 94B is shaped to permit articulation of the first assembly 80 via the pivot bearing 78.

In the embodiment of the tool 42 depicted throughout the drawings, the first assembly 80 further comprises a first shaft 96, an impactor head 98, a collar 100, and a biasing element 102. The first shaft 96 extends along the axis AX between the coupler 86 and the impactor head 98, extends through the mount aperture 94 defined in the mount body 92, and is supported for restricted movement relative to the mount 76 via the pivot bearing 78, as described in greater detail below. The impactor head 98 is fixed to the first shaft 96, is arranged to prevent the first assembly 80 from disconnecting from the mount 76, and is adapted to receive impaction force, such as via a mallet or hammer, to impact the prosthesis P into the surgical site S, as described in greater detail below.

The collar 100 is coupled to the first shaft 96 for concurrent movement, and is arranged between the mount 76 and the coupler 86. The biasing element 102, in turn, is supported about the first shaft 96 between the mount 76 and the collar 100 and is arranged to bias the first assembly 80 away from the mount 76. To this end, and according to the representative embodiment illustrated throughout the drawings, the biasing element 102 is further defined as a compression spring 102 disposed about the first shaft 96 and arranged such that the collar 100 limits movement of the spring 102 along the first shaft 96. However, those having ordinary skill in the art will appreciate that the biasing element 102 could be of any suitable type, configuration, or arrangement suitable to bias the first assembly 80 away from the mount 76 and into engagement with the second assembly 82. In some embodiments, the collar 100 is configured to lock to the first shaft 96 at different axial positions selected by the surgeon, such as to adjust preload from the biasing element 102 (not shown in detail). It will be appreciated that the collar 100 can be of any suitable type or configuration sufficient to bias the first assembly 80 away from the mount 76 and promote engagement between the coupler 86 and the receiver 88.

Figure 5:
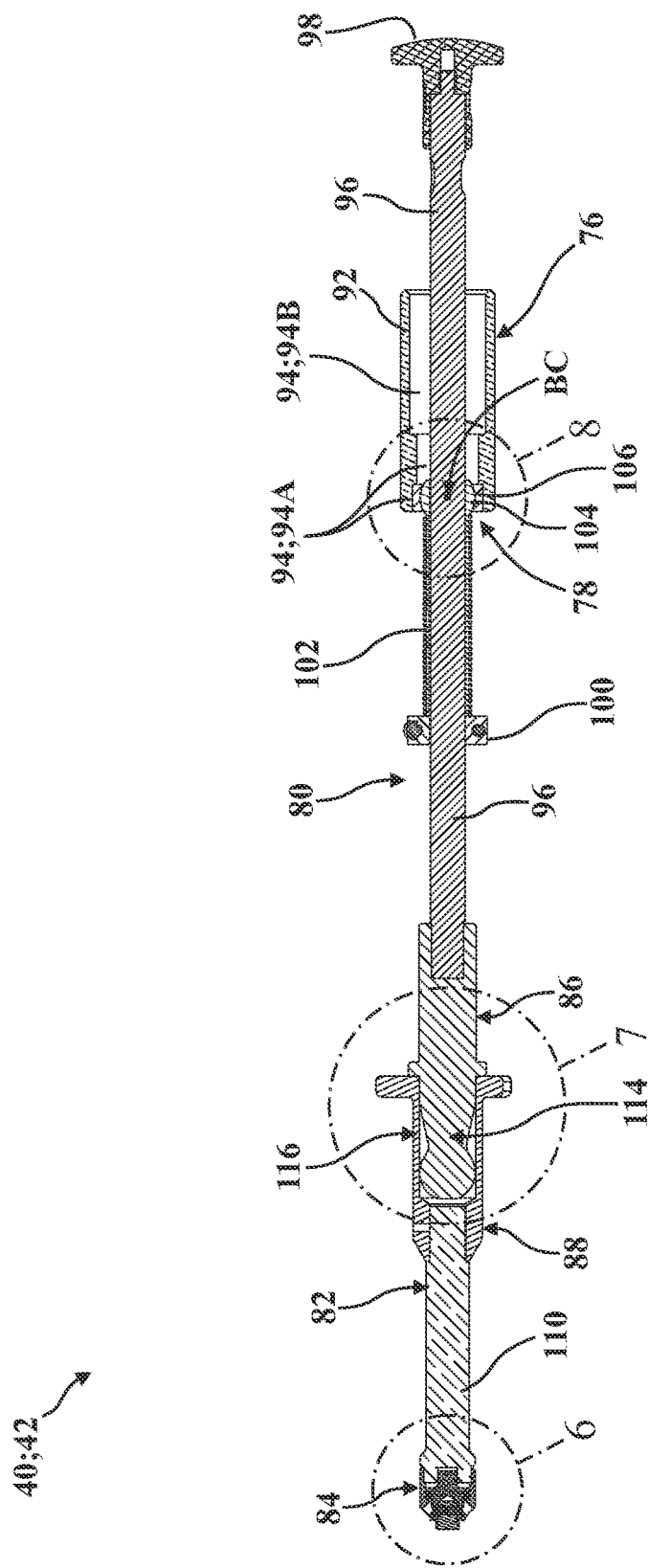
FIG. 5 is a section view taken along line 5-5 in FIG. 4.
Figure 6:
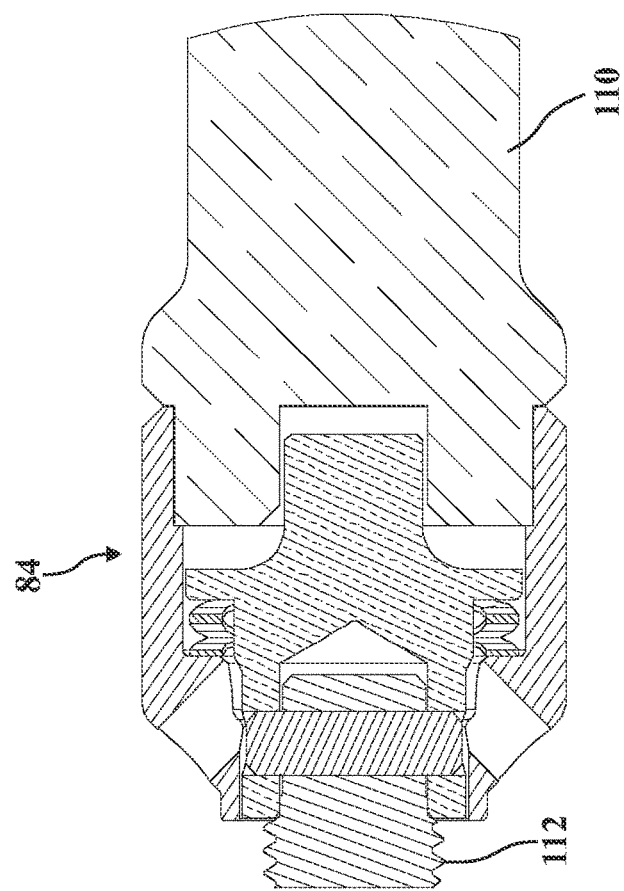
FIG. 6 is a partial, enlarged section view taken at indicia 6 in FIG. 5.
Figure 8:
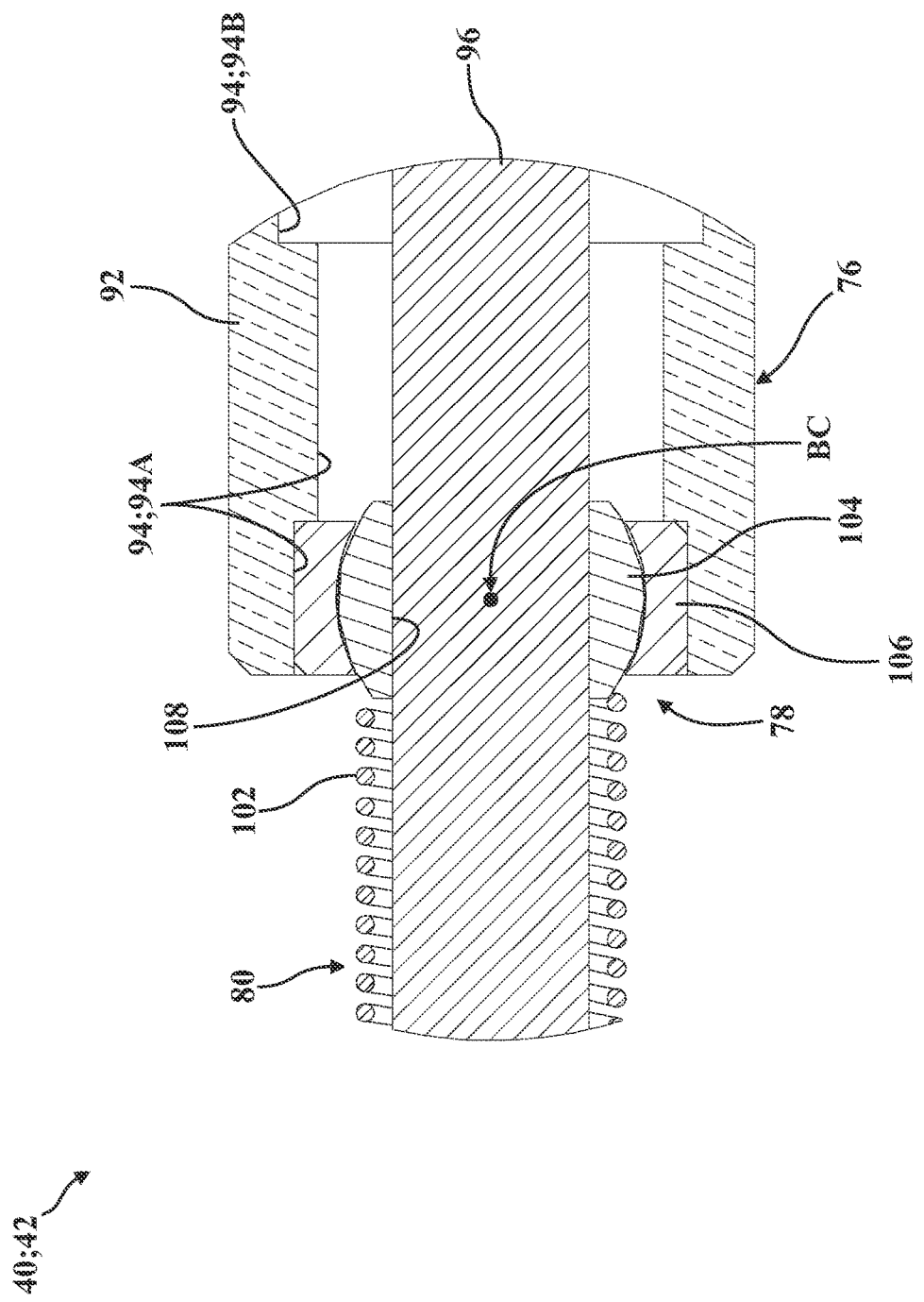
FIG. 8 is a partial, enlarged section view taken at indicia 8 in FIG. 5.

As noted above, the pivot bearing 78 supports the first shaft 96 of the first assembly 80 for rotation about the axis AX, for axial translation along the axis AX relative to the mount 76, and for at least partial articulation relative to the mount 76. To this end, and as is best shown in FIGS. 5 and 8, the representative embodiment of the pivot bearing 78 comprises an inner race 104 supported within an outer race 106. The outer race 106 is coupled to the mount body 92 of the mount 76 in the distal aperture region 94A of the mount aperture 94. The inner race 104 is arranged for movement relative to the axis AX about a bearing center point BC. More specifically, the axis AX defined by the first shaft 96 of the first assembly 80 intersects the bearing center point BC to permit angular rotation of the first assembly 80 and the inner race 104 about the bearing center point BC in a plurality of directions (see FIGS. 9A-9G). The inner race 104 of the pivot bearing 78 defines a bearing aperture 108 through which the first shaft 96 extends. In the representative embodiment of the pivot bearing 78 illustrated herein, the pivot bearing 78 is configured as a spherical plain bearing and the first assembly 80 is supported for rotation relative to the inner race 104. Put differently, the first shaft 96 of the first assembly 80 is rotatably supported by the bearing aperture 108 of the inner race 104, and the inner race 104 is similarly supported for rotation relative to the outer race 106. However, other arrangements and configurations are contemplated by the present disclosure. By way of non-limiting example, the first shaft 96 could be keyed to the inner race 104 of the pivot bearing 78 to restrict relative rotation between the inner race 104 and the first shaft 96, where relative rotation between the first assembly 80 and the mount 78 is effected by rotation of the inner race 104 within the outer race 106 and/or via rotation of the outer race 106 within the mount aperture 94 (not shown).

In the embodiment of the tool 42 depicted throughout the drawings, the second assembly 82 further comprises a second shaft 110 extending between the interface 84 and the receiver 88. As is described in greater detail below, the interface 84 is coupled to the second shaft 110 and is configured to releasably attach to the workpiece 44, such as the prosthesis P noted above, via a threaded engagement, generally indicated at 112, such that the workpiece 44 and the second assembly 82 move generally concurrently when attached together. However, it will be appreciated that the interface 84 could be configured in any suitable way sufficient to releasably attach to the workpiece 44 without departing from the scope of the present disclosure.

As noted above, the coupler 86 and the receiver 88 are employed to facilitate a releasable connection between the first assembly 80 and the second assembly 82. As will be appreciated from the subsequent description below, this configuration allows the surgeon to align the surgical robot 32 (e.g., along a predetermined impaction trajectory IT defined by or with respect to the surgical site S), position the second assembly 82 and prosthesis P at the surgical site S without necessarily moving the robotic arm 36, and subsequently bring the coupler 86 and the receiver 88 into engagement before impacting the prosthesis P along the impaction trajectory IT. While the coupler 86 and the receiver 88 are formed as discrete components which are coupled to the first shaft 96 and the second shaft 110, respectively, it will be appreciated that the coupler 86 and/or the receiver 88 could be formed integrally with or otherwise defined by other components, or could be arranged in ways. By way of non-limiting example, the coupler 86 could be formed integrally with the first shaft 96.

Figure 7:
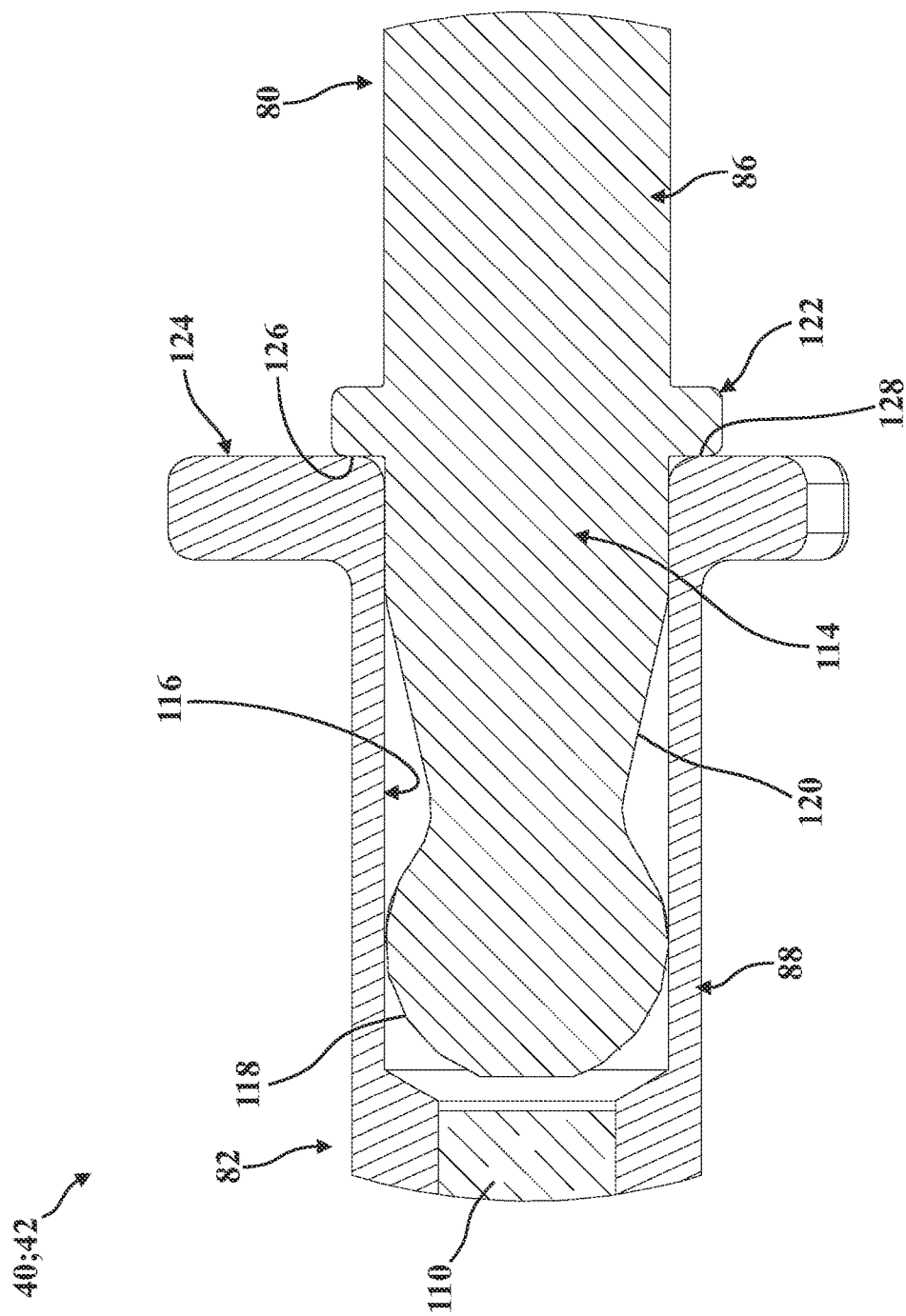
FIG. 7 is a partial, enlarged section view taken at indicia 7 in FIG. 5.

As is best depicted in FIG. 7, in the representative embodiment illustrated throughout the drawings, the coupler 86 comprises a plug 114 and the receiver 88 defines a socket 116 shaped to engage the plug 114 to align the first assembly 80 and the second assembly 82 along the axis AX. The plug 114 and the socket 116 each have generally cylindrical profiles which are shaped correspondingly to each other so as to permit relative rotation between the plug 114 and the socket 116 while, at the same time, restricting lateral movement. In the illustrated embodiment, the plug 114 can rotate freely within the socket 116 when the receiver 88 engages the coupler 86 with the first assembly 80 and the second assembly 82 aligned about the axis AX. As is described in greater detail below, because the representative embodiment of the tool 42 shown in the drawings is configured for translating impaction force applied to the first assembly 80 to the second assembly 82, relative rotation between the first and second assemblies 80, 82 is acceptable. However, depending on the specific configuration of the tool 42 and the associated surgical procedure, concurrent rotation between the first assembly 80 and the second assembly 82 may be desirable for certain applications in addition to the ability to easily disconnect the workpiece 44 and the second assembly 82 from the first assembly 80 and the surgical robot 32 via the coupler 86 and the receiver 88. By way of non-limiting illustration, the first assembly 80 could be driven by a motor and the workpiece 44 could be a reaming head, and rotation of the second assembly 82 and workpiece 44 via the motor could be effected via a lock mechanism that facilitates concurrent rotation between the first assembly 80 and the second assembly 82 (not shown). Other arrangements and configurations are contemplated.

In order to promote ease of engagement between the coupler 86 and the receiver 88 during use, the coupler 86 is further provided with an insertion portion 118 extending from the plug 114 which is shaped to guide the coupler 86 into engagement with the receiver 88. Here, the insertion portion 118 has a generally spherical profile and helps facilitate initial insertion of the coupler 86 into the receiver 88 as the insertion portion 118 enters the socket 116. The coupler 86 is also provided with a transition portion 120 extending between and merging with the plug 114 and the insertion portion 118. Here, the transition portion 120 has a generally frustoconical profile and helps guide the coupler 86 further into the receiver 88 while simultaneously bringing the plug 114 and the socket 116 into alignment with each other to effect alignment of the first assembly 80 and the second assembly 82 along the axis AX. However, those having ordinary skill in the art will appreciate that the plug 114 and/or the socket 116 could have any suitable configuration sufficient to facilitate releasable attachment of and alignment between the first assembly 80 and the second assembly 82.

In order to limit relative movement between the first assembly 80 and the second assembly 82 along the axis AX during use, in one embodiment, the coupler 86 is provided with a coupler flange 122 arranged adjacent to the plug 114, and the receiver 88 is provided with a receiver flange 124 arranged adjacent to the socket 116. The receiver flange 124 abuts the coupler flange 122 when the receiver 88 engages the coupler 86 such that the first assembly 80 cannot move further along the axis AX toward the workpiece 44. In the illustrated embodiment, the coupler 86 defines a coupler stop surface 126 and the receiver 88 defines a receiver stop surface 128 shaped to abut the coupler stop surface 126 when the receiver 88 engages the coupler 86 to limit relative movement between the first assembly 80 and the second assembly 82 along the axis AX. In the representative embodiment illustrated herein, the coupler stop surface 126 is defined by the coupler flange 122 and the receiver stop surface 128 is defined by the receiver flange 124. However, it will be appreciated that axial movement between the coupler 86 and the receiver 88 can be limited in other ways, such as without the use of discrete flanges.

As noted above, the tool 42 generally facilitates positioning the workpiece 32 with the surgical robot 32 and helps guide the workpiece 44 to the target 46 and, more specifically, the embodiment of the tool 42 depicted throughout the drawings is adapted to impact the prosthesis P guided by the surgical robot 32 into the surgical site S. Thus, in some embodiments, the workpiece 44 is further defined as the prosthesis P, the target 46 is further defined as the surgical site S, and the tool 42 is adapted to impact the prosthesis P guided by the surgical robot 32 along the impaction trajectory IT into the surgical site S. In these embodiments, the first assembly 80 may be further defined as a driver assembly 80, the second assembly 82 may be further defined as an impactor assembly 82, and the interface 84 is adapted to attach to the prosthesis P such that force applied to the driver assembly 80 urges the prosthesis P into the surgical site S, as described in greater detail below in connection with FIGS. 9A-9G. However, it will be appreciated that the first assembly 80, the second assembly 82, the workpiece 44, and/or the target 46 can be configured or otherwise defined here in any suitable way sufficient to align the first assembly 80 and the second assembly 82 together along the axis AX to facilitate positioning the workpiece 44 with the surgical robot 32.

Figure 9A:
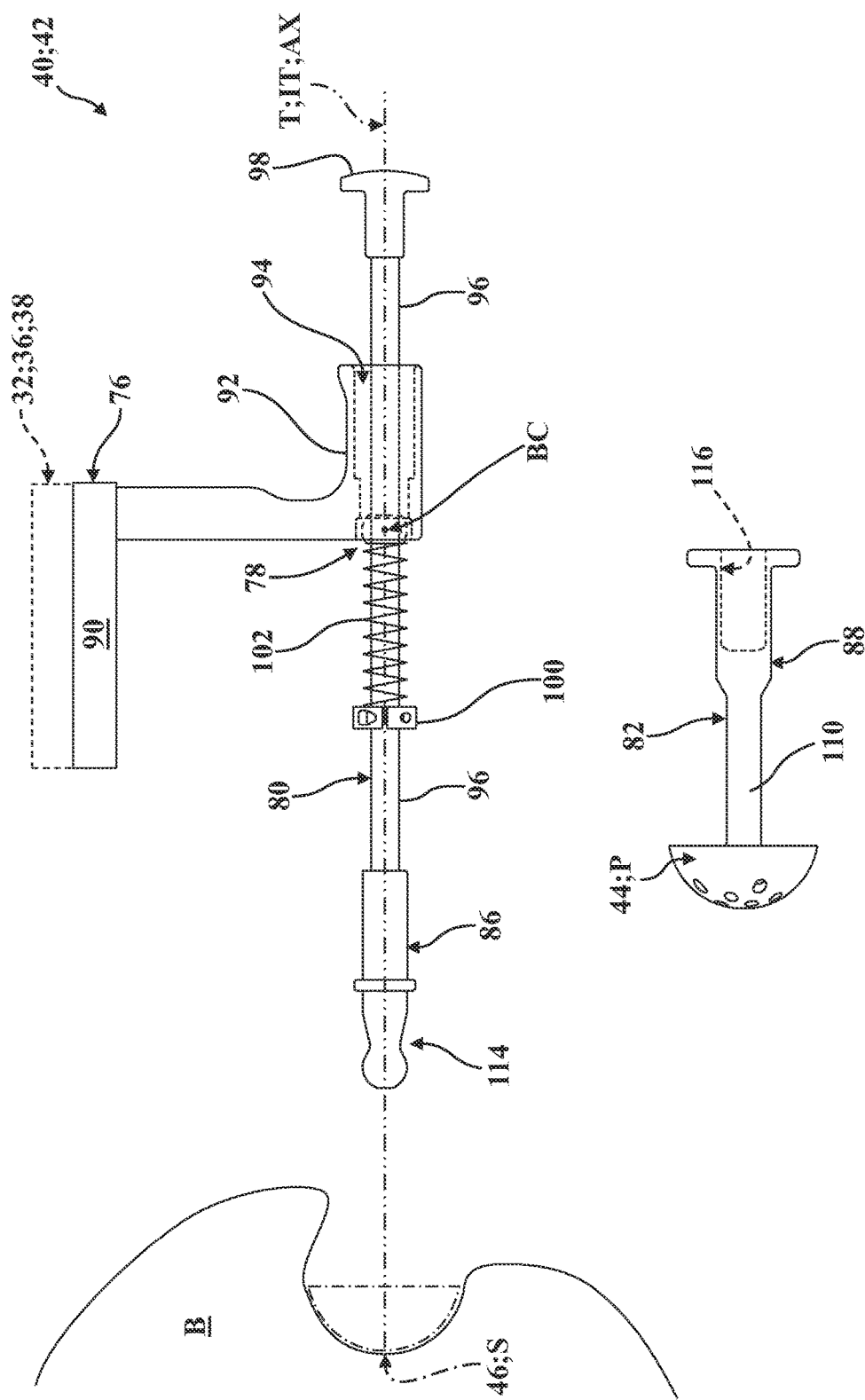
FIG. 9A is an illustrative schematic view of the tool of FIGS. 1A-3, shown with a pivot bearing coupled to the mount and supporting the first assembly, the first assembly having a coupler and defining an axis aligned with a surgical site, and shown with the second assembly attached to the prosthesis and having a receiver spaced from the surgical site and from the first assembly.
Figure 9B:
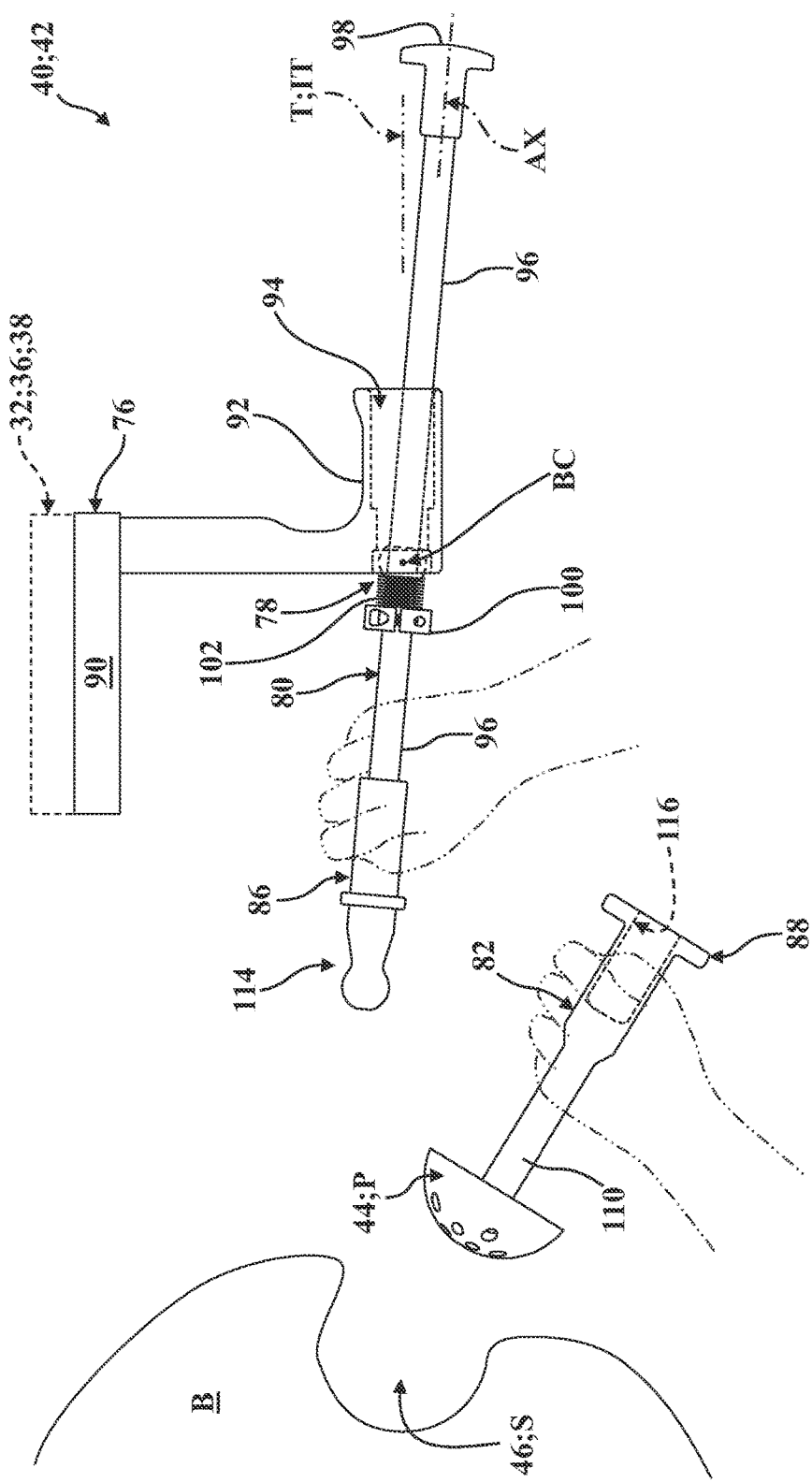
FIG. 9B is another illustrative schematic view of the tool, prosthesis, and surgical site of FIG. 9A, shown with the first assembly articulated and translated relative to the mount about the pivot bearing, and with the prosthesis and second assembly positioned adjacent to the surgical site.

Referring now to FIGS. 9A-9G, certain steps for utilizing the tool 42 to impact the prosthesis P into the surgical site S are shown sequentially. In FIG. 9A, the mount 76 and the first assembly 80 of the tool 42 are positioned adjacent to the surgical site S along an impaction trajectory IT aligned with the axis AX defined by the first shaft 96. Here, as noted above, the impaction trajectory IT can be defined, determined, or otherwise set in a number of different ways, such as based on the intended position of the prosthesis P after being implanted into the acetabulum, which is shown in phantom in FIG. 9A and which is aligned to the axis AX. As is depicted generically in FIGS. 9A-9G, portions of the patient's body B adjacent the surgical site S such as muscle, cartilage, portions of the pelvic bone, and the like may limit the surgeon's ability to position the prosthesis P at the surgical site S prior to impaction where the prosthesis P is otherwise moved by the surgical robot 32. Here, the tool 42 of the present disclosure allows the surgeon to approach and initially position the prosthesis P at the surgical site S without necessitating a large incision or excessive bone/tissue removal at the surgical site S which might otherwise be required. Moreover, the tool 42 of the present disclosure also allows the surgeon to set the surgical robot 32 to maintain the impaction trajectory IT and approach the surgical site S with the prosthesis P without necessarily requiring further manipulation of the robotic arm 36. This also allows the surgeon to minimize manipulation to the patient's body B to facilitate approach of the surgical site S with the prosthesis P.

Figure 9C:
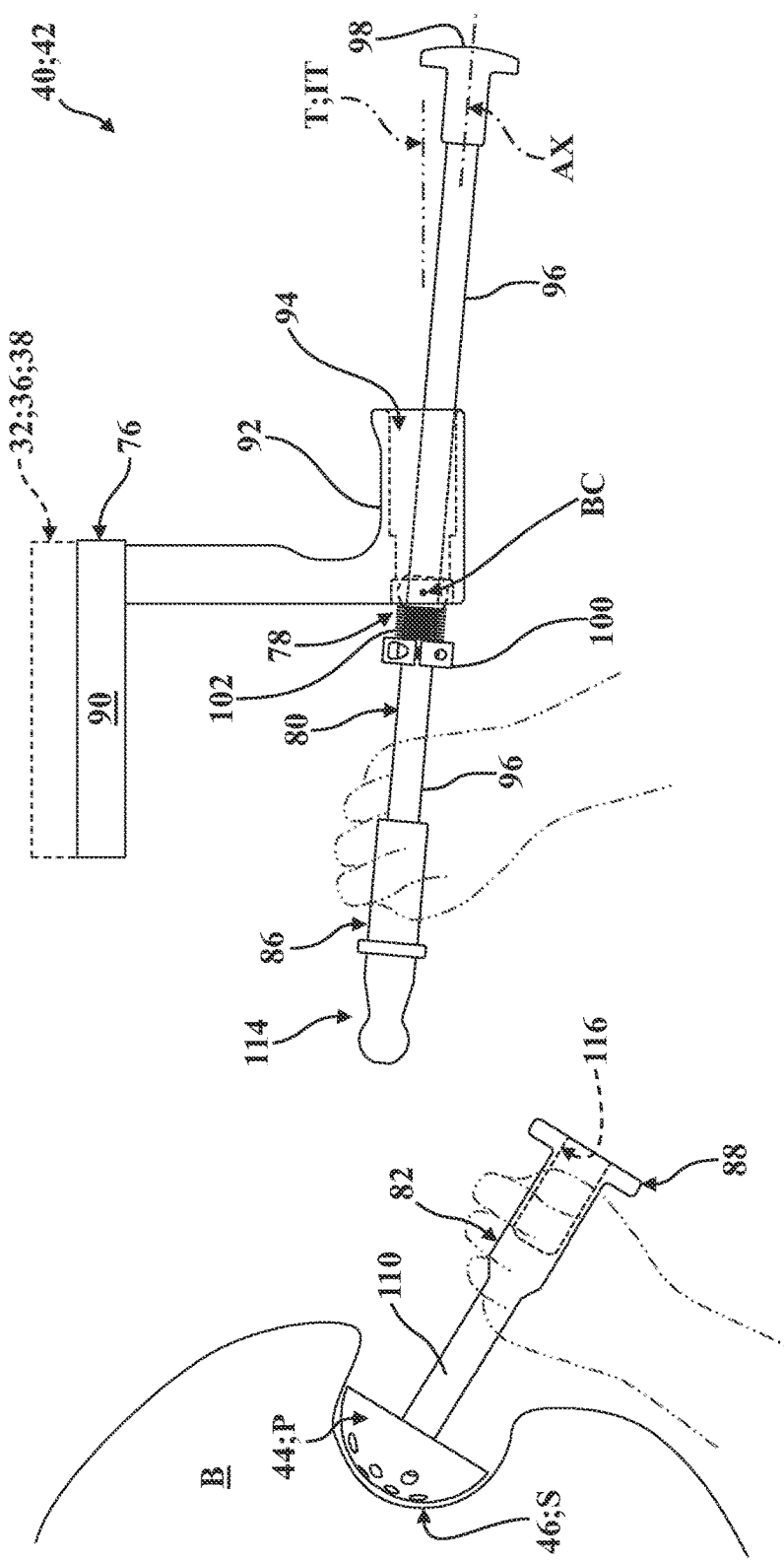
FIG. 9C is another illustrative schematic view of the tool, prosthesis, and surgical site of FIGS. 9A-9B, shown with the prosthesis and second assembly positioned at the surgical site.
Figure 9D:
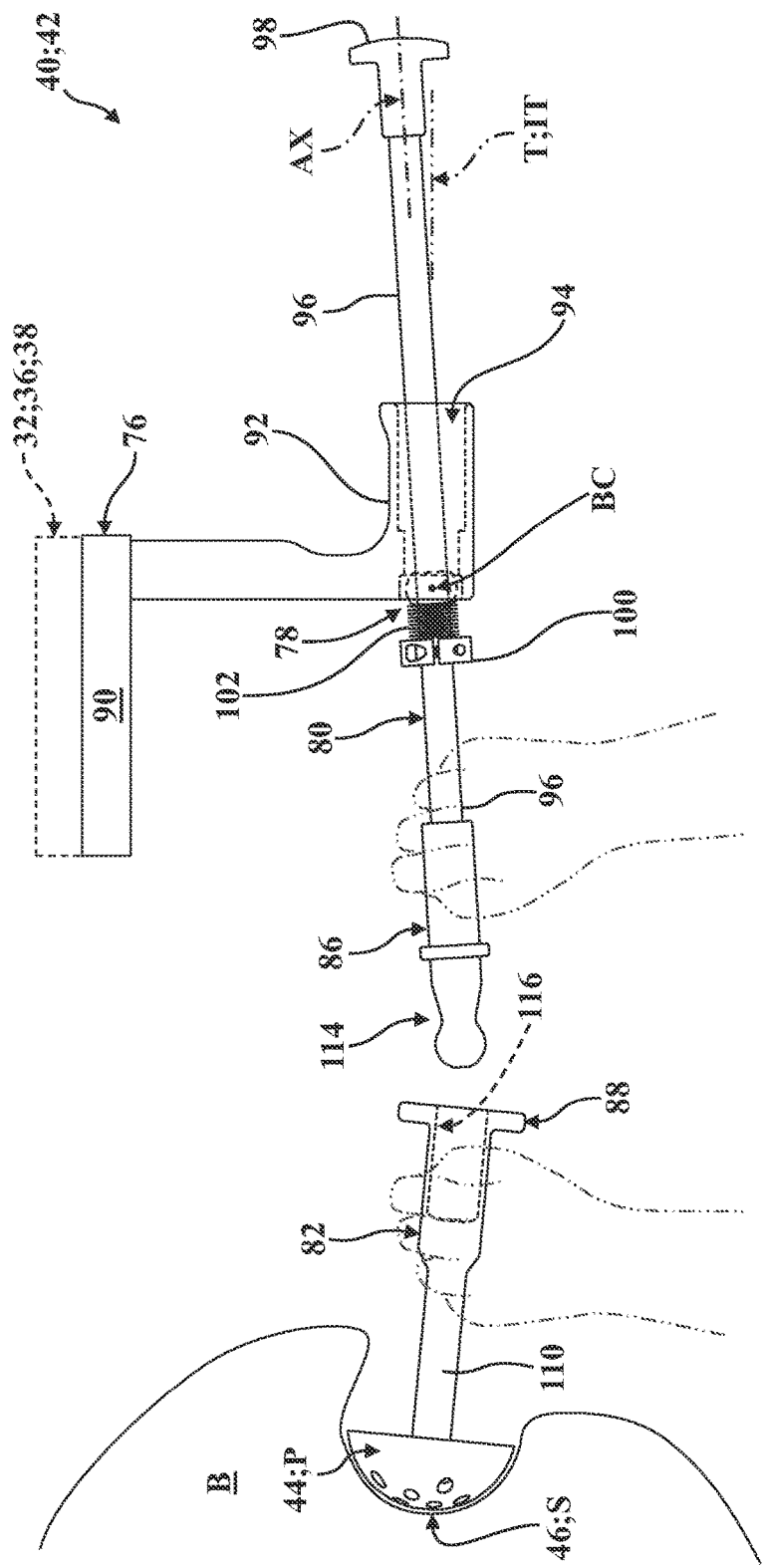
FIG. 9D is another illustrative schematic view of the tool, prosthesis, and surgical site of FIGS. 9A-9C, shown with the first and second assemblies articulated towards each other and with the coupler positioned adjacent to the receiver.
Figure 9E:
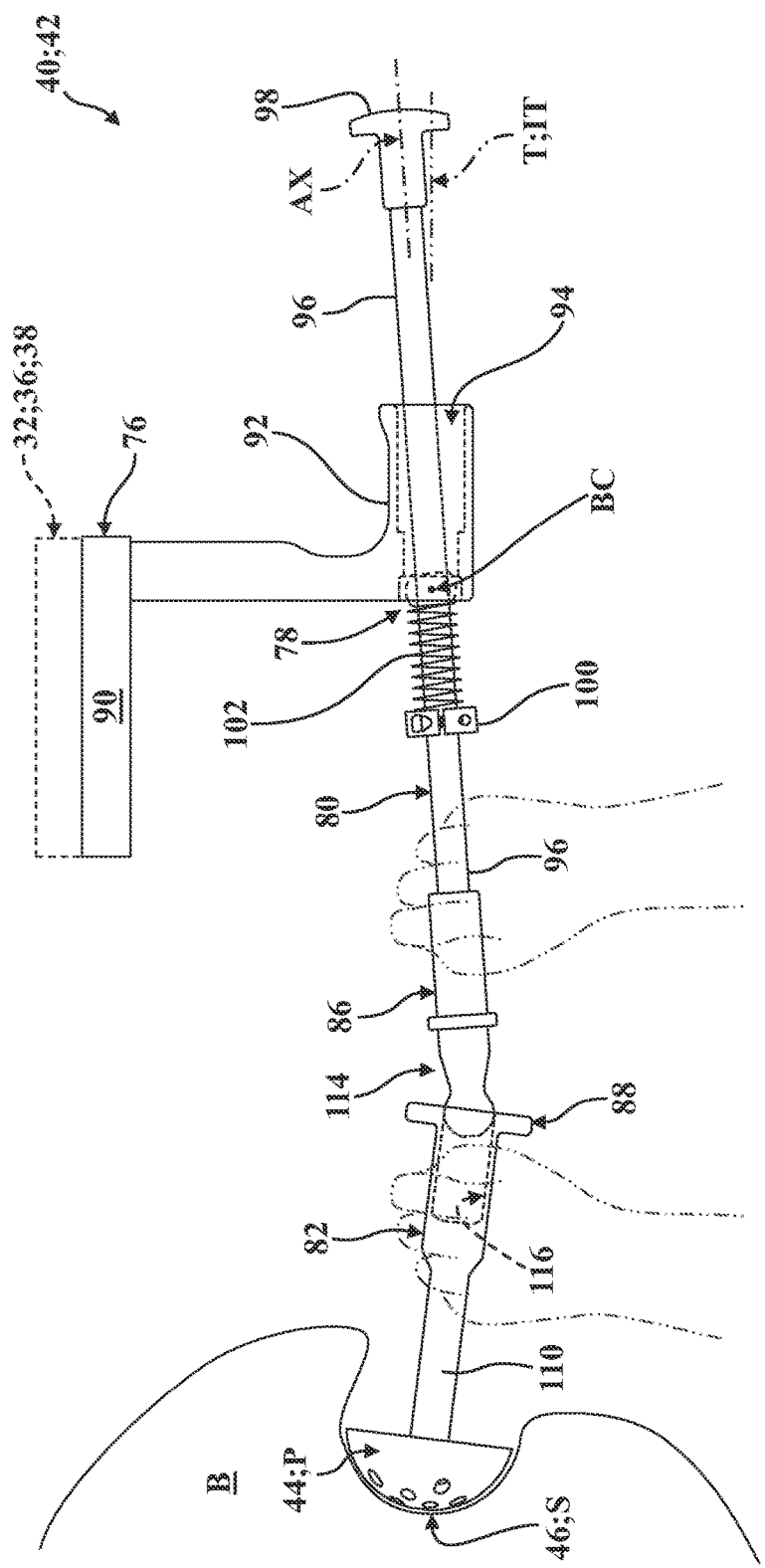
FIG. 9E is another illustrative schematic view of the tool, prosthesis, and surgical site of FIGS. 9A-9D, shown with the coupler partially inserted into the receiver.
Figure 9F:
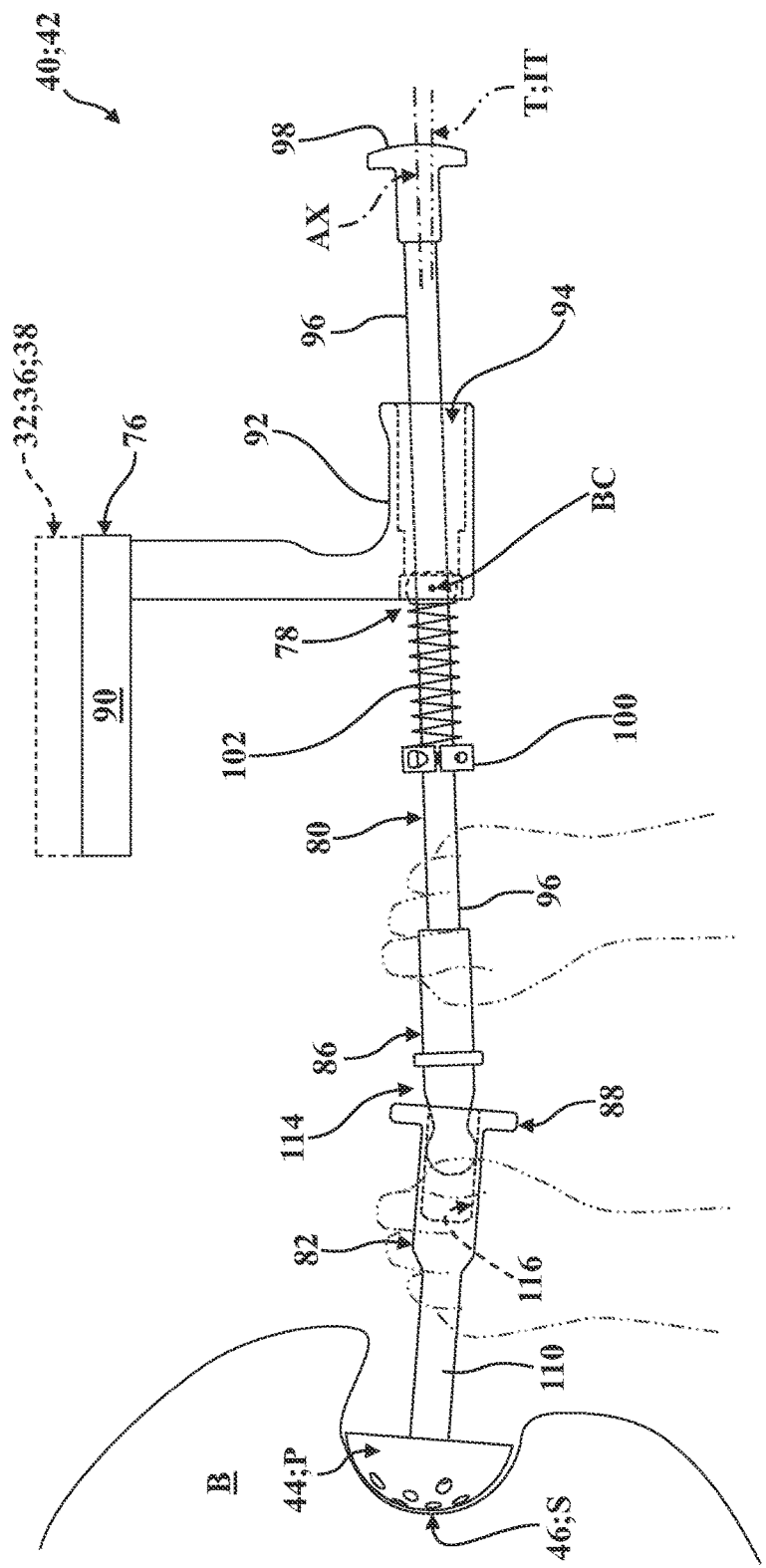
FIG. 9F is another illustrative schematic view of the tool, prosthesis, and surgical site of FIGS. 9A-9E, shown with the coupler inserted further into the receiver.
Figure 9G:
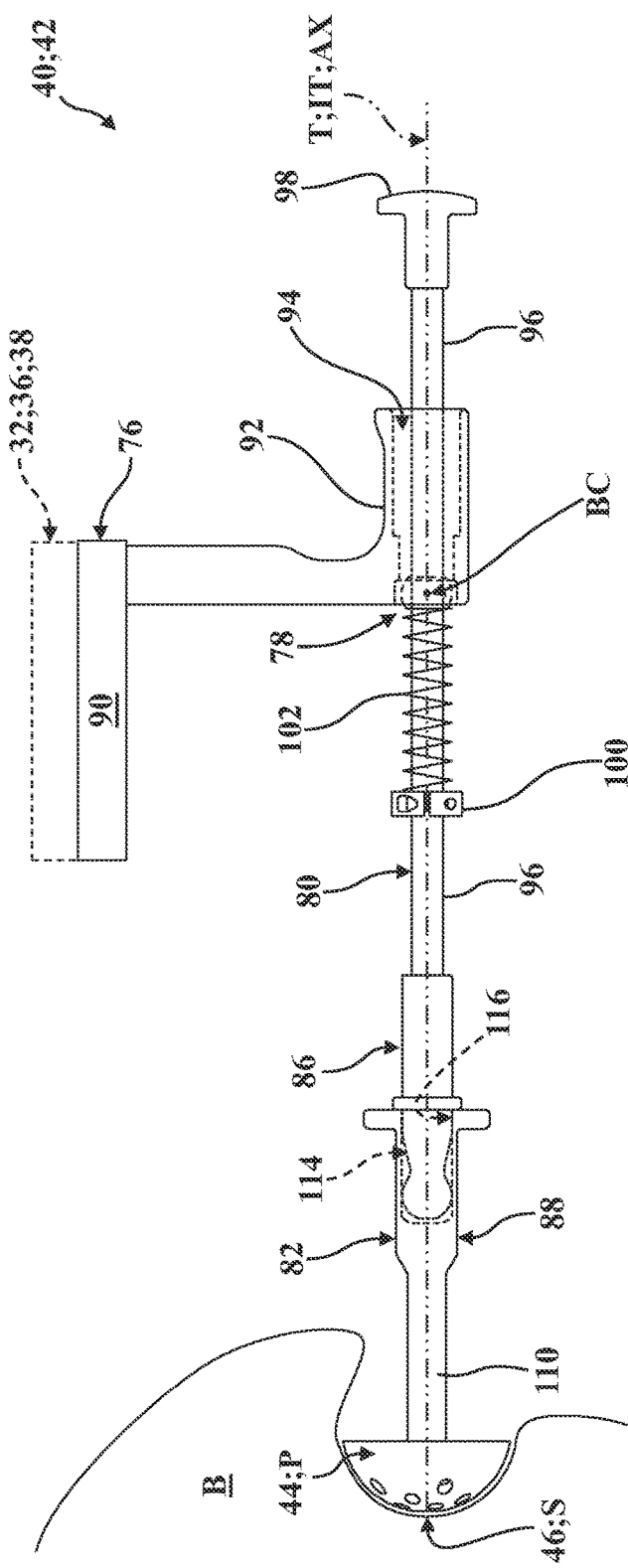
FIG. 9G is another illustrative schematic view of the tool, prosthesis, and surgical site of FIGS. 9A-9F, shown with the coupler engaging the receiver to align the second assembly and the first assembly with the axis.

With continued reference to FIG. 9A, as noted above, the mount 76 and the first assembly 80 of the tool 42 are positioned along the impaction trajectory IT aligned with the axis AX and the prosthesis P. The second assembly 82 is not yet placed at the surgical site S. Once the impaction trajectory IT is determined or otherwise set, the surgical robot 32 can maintain the position and orientation of the mount 76 relative to the surgical site S while the surgeon subsequently moves the first assembly 80 along the axis AX against the biasing element 102 and about the bearing center point BC and approaches the surgical site with the prosthesis P and the second assembly 82 (see FIG. 9B). As shown in FIG. 9C, the prosthesis P and second assembly 82 can be moved toward the surgical site without necessitating movement of the mount 76 (compare FIG. 9C with FIG. 9B). Once the surgeon has approached the surgical site S with the prosthesis P, the first assembly 80 can rotate about and translate along the axis AX through the bearing center point BC as the coupler 86 and the receiver 88 are moved towards each other (see FIG. 9D; compare FIG. 9D with FIG. 9C). Next, as shown in FIG. 9E, the insertion portion 118 of the coupler 86 is positioned into the socket 116 of the receiver 88 as the first assembly 80 and the second assembly 82 move into alignment with each other about the axis AX. In FIG. 9F, the coupler 86 and the receiver 88 are moved closer toward each other, with the transition portion 120 of the coupler 86 guiding the plug 114 into alignment with the socket 116 as the first assembly 80 and the second assembly 82 move closer into alignment with each other about the axis AX. In FIG. 9G, the first assembly 80 and the second assembly 82 are each aligned with the axis AX which, in turn, is aligned to the impaction trajectory IT. Here, the plug 114 of the coupler 86 is shown seated in the socket 116 of the receiver 88 with the coupler stop surface 126 abutting the receiver stop surface 128 to limit axial movement of the first assembly 80 further toward the second assembly 82. It will be appreciated that the biasing element 102 is compressed slightly in FIG. 9G, which helps prevent inadvertent disengagement between the coupler 86 and the receiver 88 during use. Further, it will be appreciated that compression of the biasing element 102 which occurs as the first assembly 80 and second assembly 82 are orientated towards each other, helps to urge the plug 114 into the socket 116 by axially biasing the coupler 86 towards the receiver 88 (see FIGS. 9D-9G).

Figure 10A:
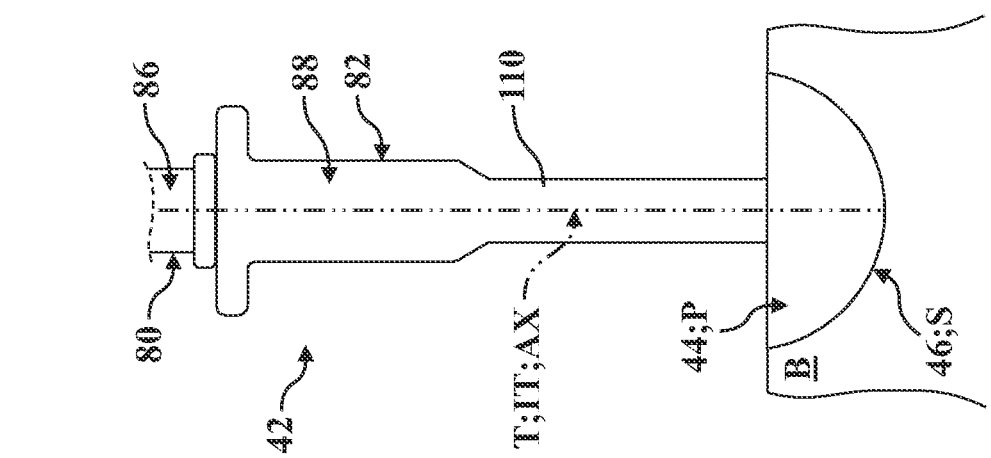
FIG. 10A is a partial schematic view of the first assembly of the tool of FIGS. 9A-9G, shown spaced from and properly aligned with a surgical site.
Figure 10B:
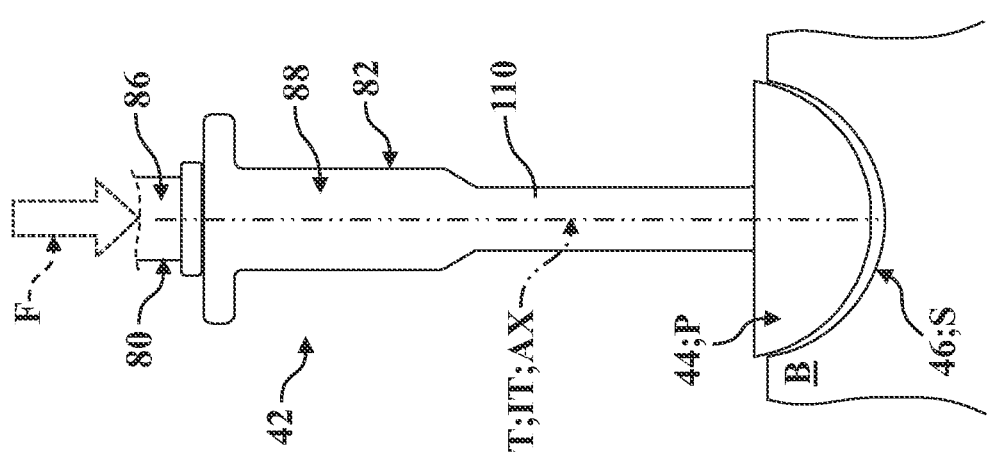
FIG. 10B is a partial schematic view of the first assembly of FIG. 10A, shown attached to the second assembly and the prosthesis of FIGS. 9A-9G, with the prosthesis positioned at and properly aligned with the surgical site, and with an illustratively-depicted impact force properly applied along the axis.
Figure 10C:
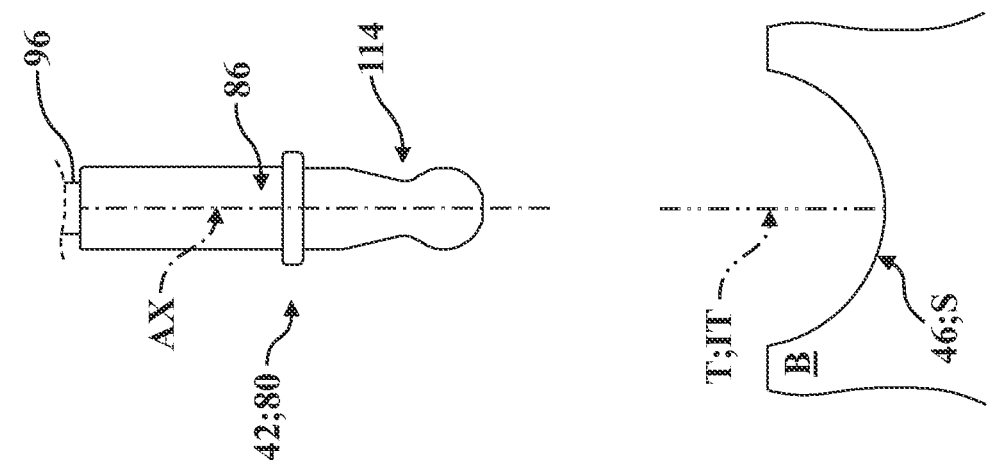
FIG. 10C is another partial schematic view of the tool and prosthesis of FIG. 10B, shown with the prosthesis properly impacted into the surgical site.
Figure 11C:
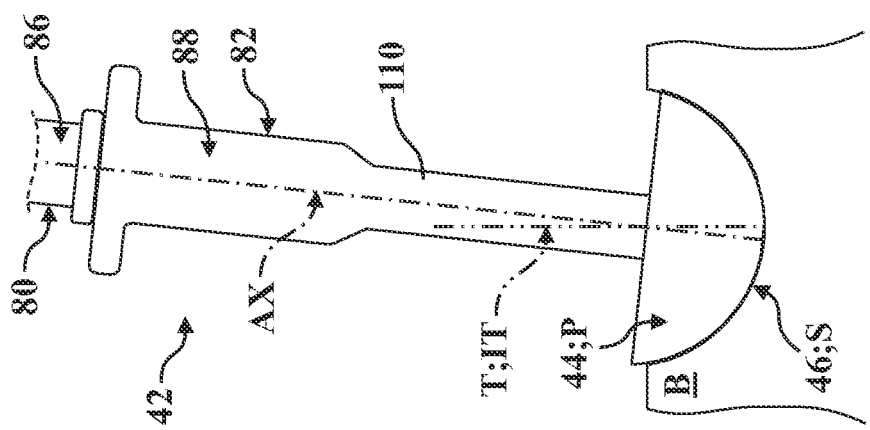
FIG. 11C is another partial schematic view of the tool and prosthesis of FIG. 11B, shown with the prosthesis improperly impacted into the surgical site.
Figure 11B:
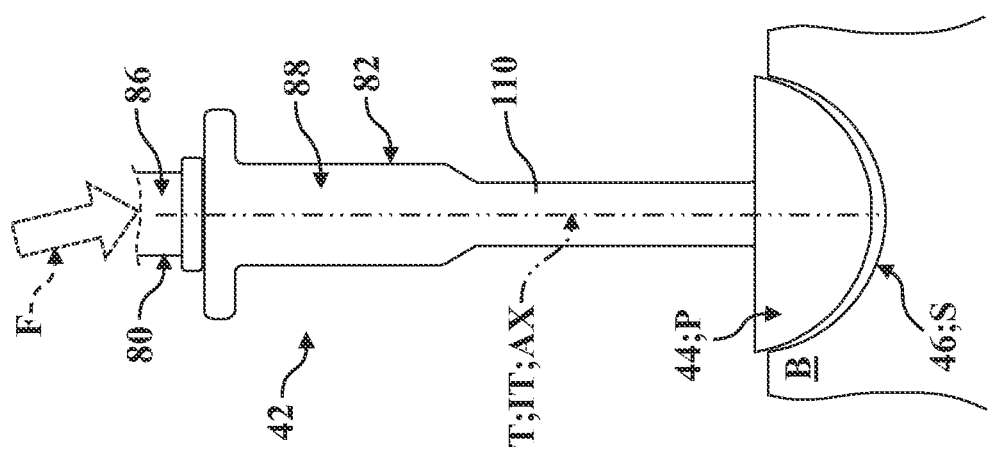
FIG. 11B is a partial schematic view of the first assembly of FIG. 11A, shown attached to the second assembly and the prosthesis of FIGS. 9A-9G, with the prosthesis positioned at and properly aligned with the surgical site, and with an illustratively-depicted impact force improperly applied along the axis.
Figure 11A:
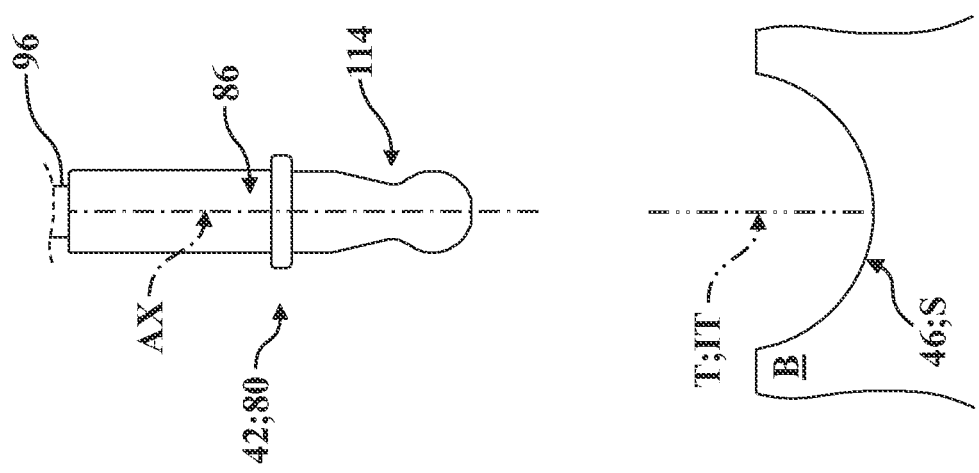
FIG. 11A is a partial schematic view of the first assembly of the tool of FIGS. 9A-9G, shown spaced from and properly aligned with a surgical site.
Figure 12C:
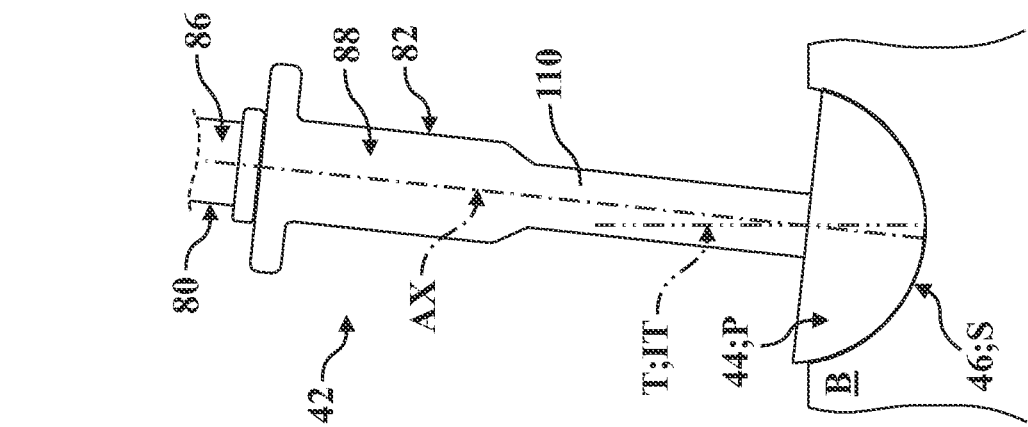
FIG. 12C is another partial schematic view of the tool and prosthesis of FIG. 12B, shown with the prosthesis improperly impacted into the surgical site.
Figure 12B:
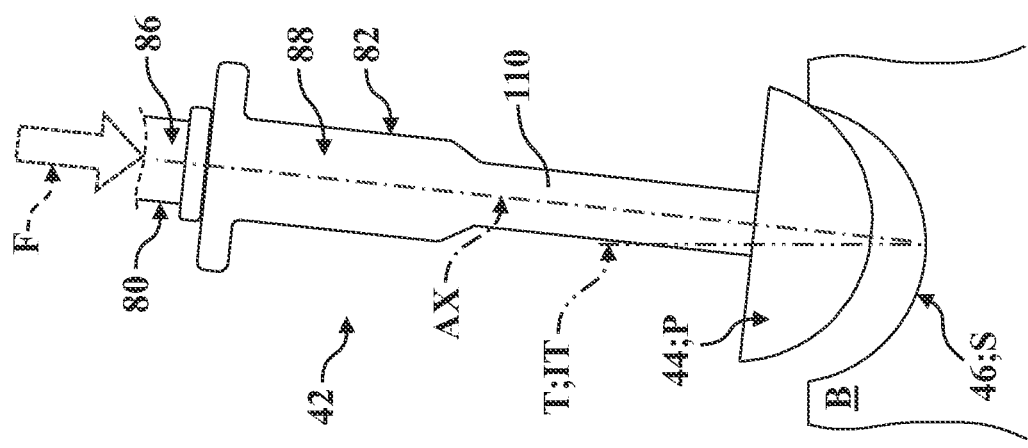
FIG. 12B is a partial schematic view of the first assembly of FIG. 12A, shown attached to the second assembly and the prosthesis of FIGS. 9A-9G, with the prosthesis positioned at and improperly aligned with the surgical site, and with an illustratively-depicted impact force properly applied along the axis.
Figure 12A:
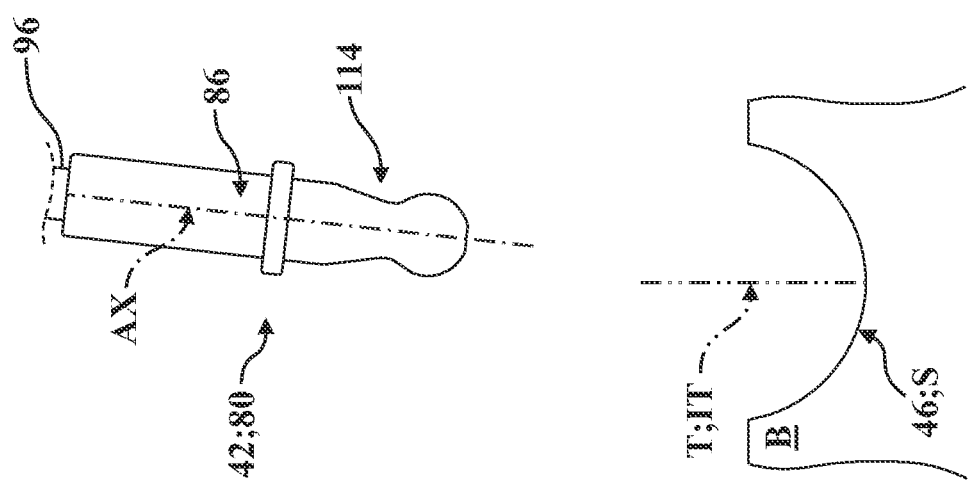
FIG. 12A is a partial schematic view of the first assembly of the tool of FIGS. 9A-9G, shown spaced from and improperly aligned with a surgical site.

Referring now to FIGS. 10A-12C, as noted above, the reamed acetabulum at the surgical site S generally defines the impaction trajectory IT to which the axis AX is aligned prior to impaction in order to ensure that the prosthesis P is implanted correctly. FIGS. 10A-10C sequentially depict certain steps associated with proper implantation. In FIG. 10A, the first assembly 80 of the tool 42 is shown spaced from the surgical site S and aligned to the axis AX which, in turn, is properly aligned with the impaction trajectory IT. FIG. 10B shows the prosthesis P, the second assembly 82, and a portion of the first assembly 80 at the surgical site S with the axis AX properly aligned with the impaction trajectory IT, and schematically depicts an impact force F applied properly to the first assembly 80 along the axis AX, resulting such as from force applied to the impactor head 98 of the first assembly 80 (see FIGS. 2-3) via a mallet (not shown). FIG. 10C shows the properly-implanted prosthesis P resulting from the proper application of impact force F along the axis AX and from the proper alignment between the axis AX and the impaction trajectory IT. However, those having ordinary skill in the art will appreciate that the application of impact force F can sometimes occur in a way that which does not translate perfectly along the axis AX. Here, as is depicted in FIGS. 11A-11C, even where the axis AX is properly aligned to the impaction trajectory IT (see FIG. 11A), improper application of impact force F (see FIG. 11B; compare to FIG. 10B) can be problematic and may result in damage to one or more of the prosthesis P, the tool 42, and/or the surgical robot 32, as well as improper implantation of the prosthesis P (see FIG. 11C). Similarly, as is depicted in FIGS. 12A-12C, improper alignment of the axis AX relative to the impaction trajectory IT (see FIG. 12A; compare to FIG. 10A) can likewise result in damage to one or more of the prosthesis P, the tool 42, and/or the surgical robot 32, as well as improper implantation of the prosthesis P (see FIG. 12C), even where the impact force F is properly applied along the axis AX (see FIG. 12B).

In order to overcome the disadvantages described above in connection with improper implantation of the prosthesis P, the present disclosure is also directed toward a compliance mechanism, generally indicated at 130 in FIGS. 13A-13B and 14B-19C. Here, the compliance mechanism 130 is interposed between the prosthesis P and the second assembly 82, and has a proximal body 132 adapted to couple to the interface 84 and a distal body 134 adapted to attach to the prosthesis P. As is described in greater detail below, the proximal body 132 supports the distal body 134 for movement about a remote point RP along the axis AX to guide the prosthesis P into alignment with the surgical site S in response to impact force F applied to the first assembly 80 along the axis AX. As is depicted schematically in FIGS. 13A-13B, movement of the distal body 134 and the prosthesis P occurs concurrently about the remote point along the axis AX, whereas the proximal body 132 remains secured to the second assembly 82. Here, because the remote point RP remains aligned with the axis AX, impact force F applied along the axis AX has a tendency to "pull" the prosthesis into surgical site S, thereby promoting implantation of the prosthesis P even in the face of misalignment between the axis AX and the impaction trajectory IT and/or improper application of impact force I, as described in greater detail below.

As noted previously, while the representative embodiment of the tool 42 described and illustrated herein is configured for use in impacting the prosthesis P into the surgical site S, the alignment and releasable attachment advantages afforded by the coupler 86 and the receiver 88 can be used in connection with any suitable type of tool 42 used to position any suitable type of workpiece 44 with the surgical robot 32. Here too, as will be appreciated from the subsequent description below, the compliance mechanism 130 is not limited for use with impacting prostheses P and can be used to guide any suitable type of workpiece 44 supported for movement about the remote point RP along the axis AX into alignment with the target 46 (e.g., along or with respect to a trajectory T maintained by the surgical robot 32) as the tool 42 directly or indirectly moves the workpiece 44.

Like FIGS. 12A-12C, FIGS. 14A-14C similarly depict certain steps involved in implanting the prosthesis P to the surgical site S where there is improper alignment of the axis AX relative to the impaction trajectory IT. Here, however, the compliance mechanism 130 is interposed between the prosthesis P and the interface 84 (depicted schematically in FIGS. 14B-14C) of the second assembly 82 to permit movement about the remote point RP, as noted above. Despite the misalignment between the axis AX and the impaction trajectory IT which causes the prosthesis P to engage the surgical site S unevenly (see FIG. 14B), the compliance mechanism 130 allows the prosthesis P to be implanted properly (see FIG. 14C). While the physical contact between the prosthesis P and the surgical site S caused by the impaction force F depicted in FIG. 14B would typically result in an opposing reactive force that could damage the surgical site S, the tool 42, the prosthesis P, and/or the surgical robot 32, the presence of the compliance mechanism 130 effectively "pulls" the prosthesis P towards the remote point RP as the impact force F is applied. This, as well as the generally spherical profile of the prosthesis P and the reamed acetabulum, promotes proper impaction of the prosthesis P into the surgical site S despite the misalignment between the axis AX and the impaction trajectory IT (see FIG. 14C).

Referring now to FIGS. 15A-15B, different embodiments of the compliance mechanism 130 are schematically illustrated. In FIG. 15A, the proximal body 132 and the distal body 134 have spherical faces that slidably contact each and define the location of the remote point RP along the axis AX. In FIG. 15B, the compliance mechanism is configured according to the teachings of U.S. Pat. No. 4,098,001, the disclosure of which is hereby incorporated by reference in its entirety. Different configurations and embodiments of the compliance mechanism 130 are contemplated.

Figure 14A:
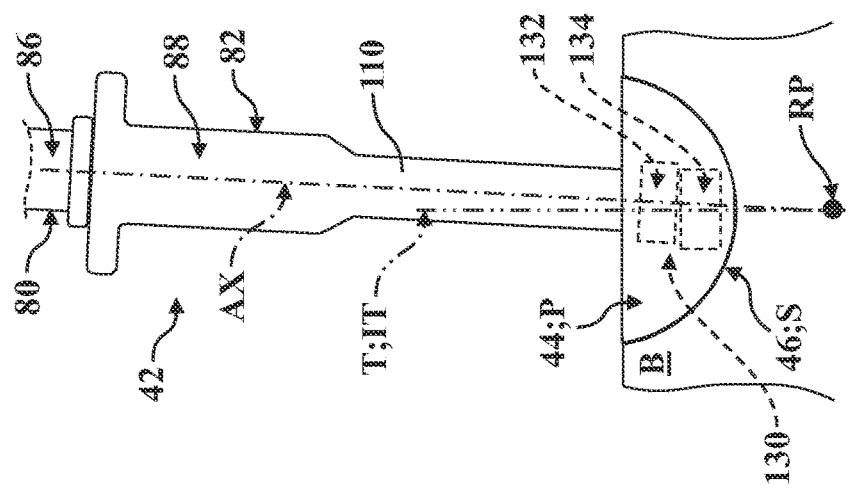
FIG. 14A is a partial schematic view of the first assembly of the tool of FIGS. 9A-9G, shown spaced from and improperly aligned with a surgical site.
Figure 14B:
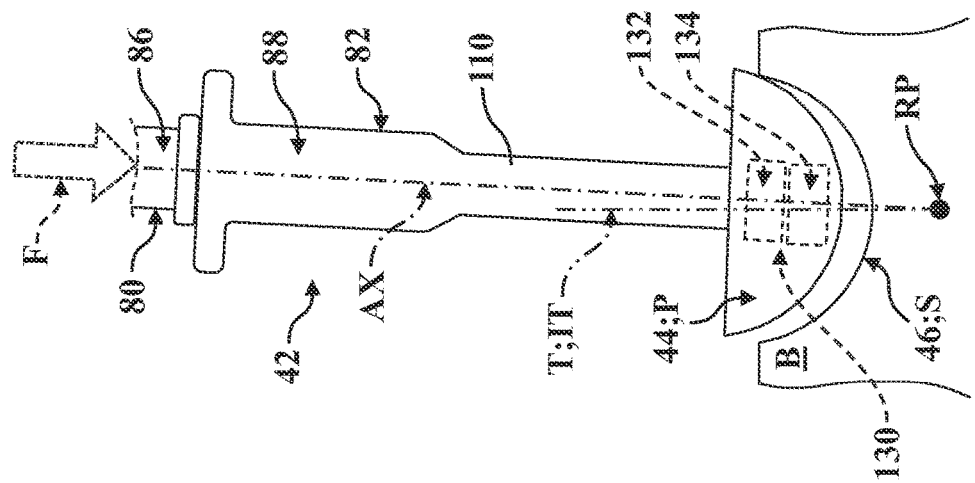
FIG. 14B is a partial schematic view of the first assembly of FIG. 14A, shown attached to the second assembly, the compliance mechanism, and the prosthesis of FIGS. 13A-13B, with the prosthesis positioned at and improperly aligned with the surgical site, and with an illustratively-depicted impact force properly applied along the axis.
Figure 14C:
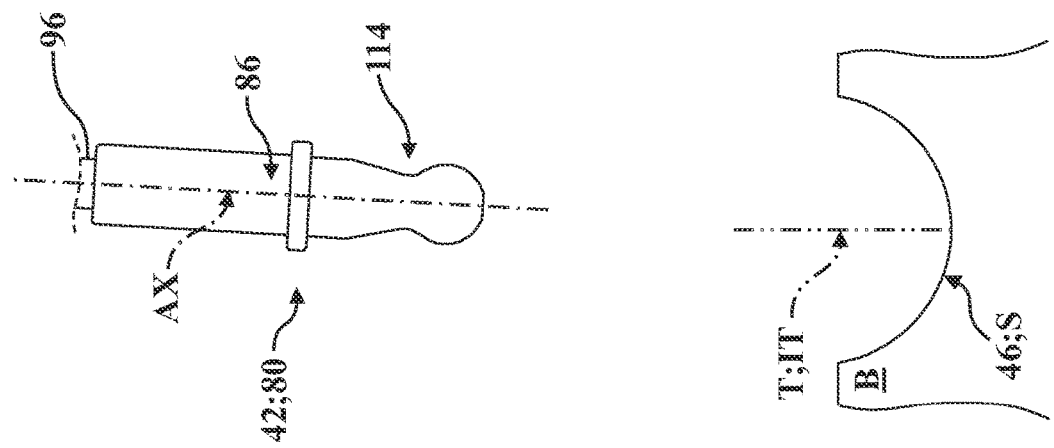
FIG. 14C is another partial schematic view of the tool, the compliance mechanism, and the prosthesis of FIG. 14B, shown with the prosthesis properly impacted into the surgical site resulting from movement of the prosthesis about a remote point defined by the compliance mechanism.
Figure 16:
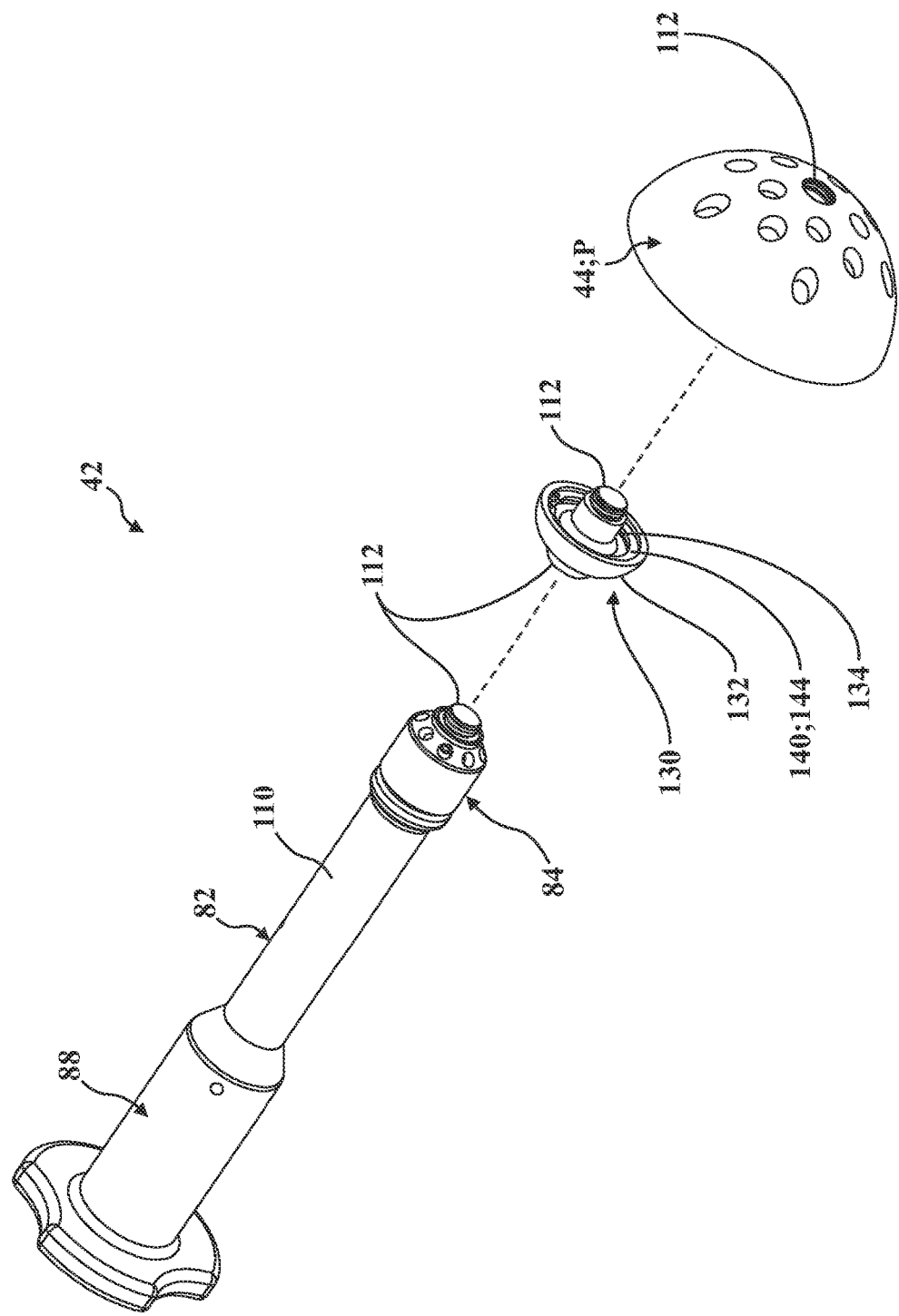
FIG. 16 is an exploded perspective view showing a portion of the tool, the prosthesis, and one embodiment of the compliance mechanism depicted in FIGS. 13A-13B.
Figure 19A:
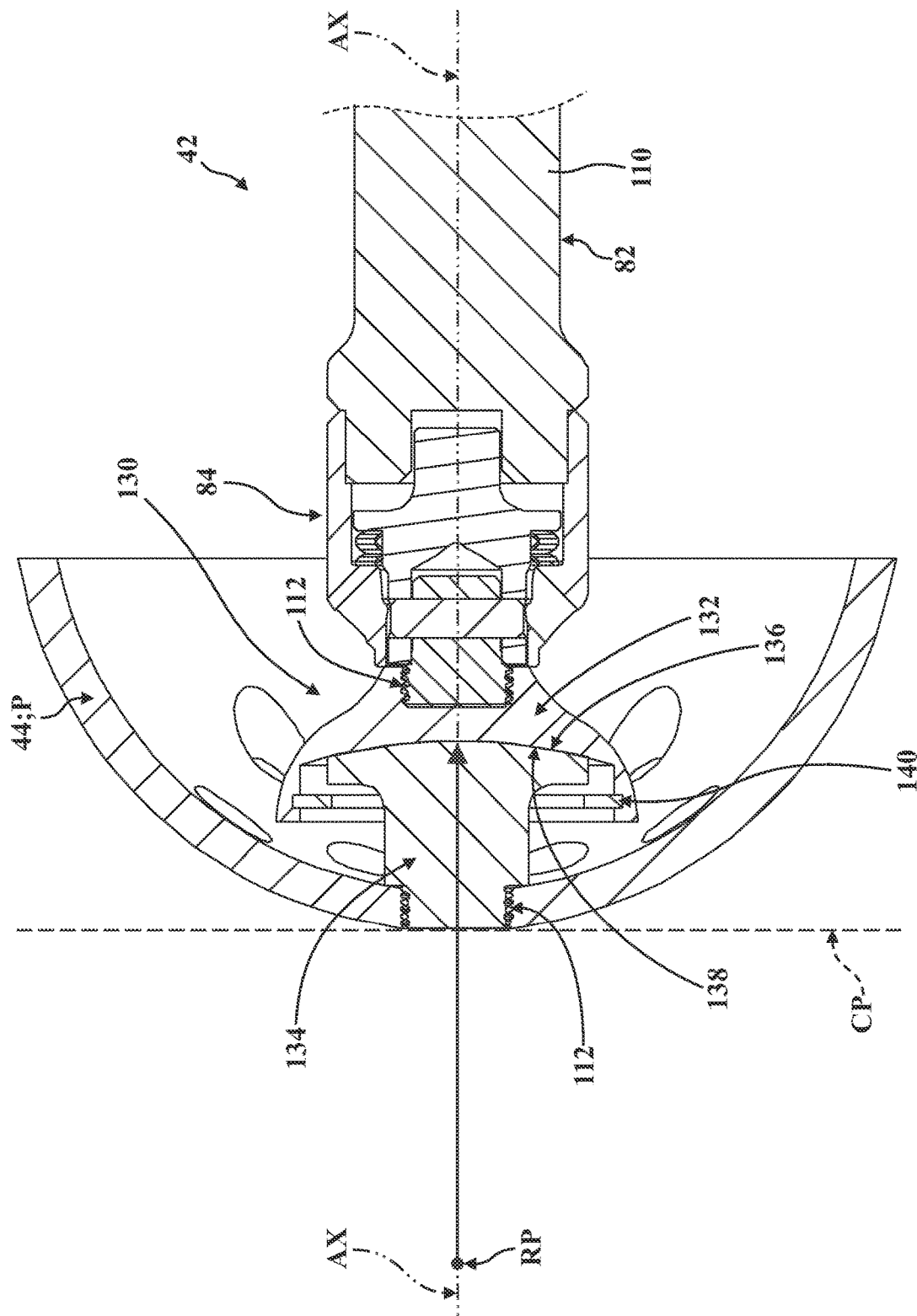
FIG. 19A is a partial section view taken through the prosthesis, a portion of the tool, and the compliance mechanism depicted in FIG. 16, shown with the prosthesis aligned with the axis defined by the tool, and with the remote center defined by the compliance mechanism aligned about the axis.
Figure 19B:
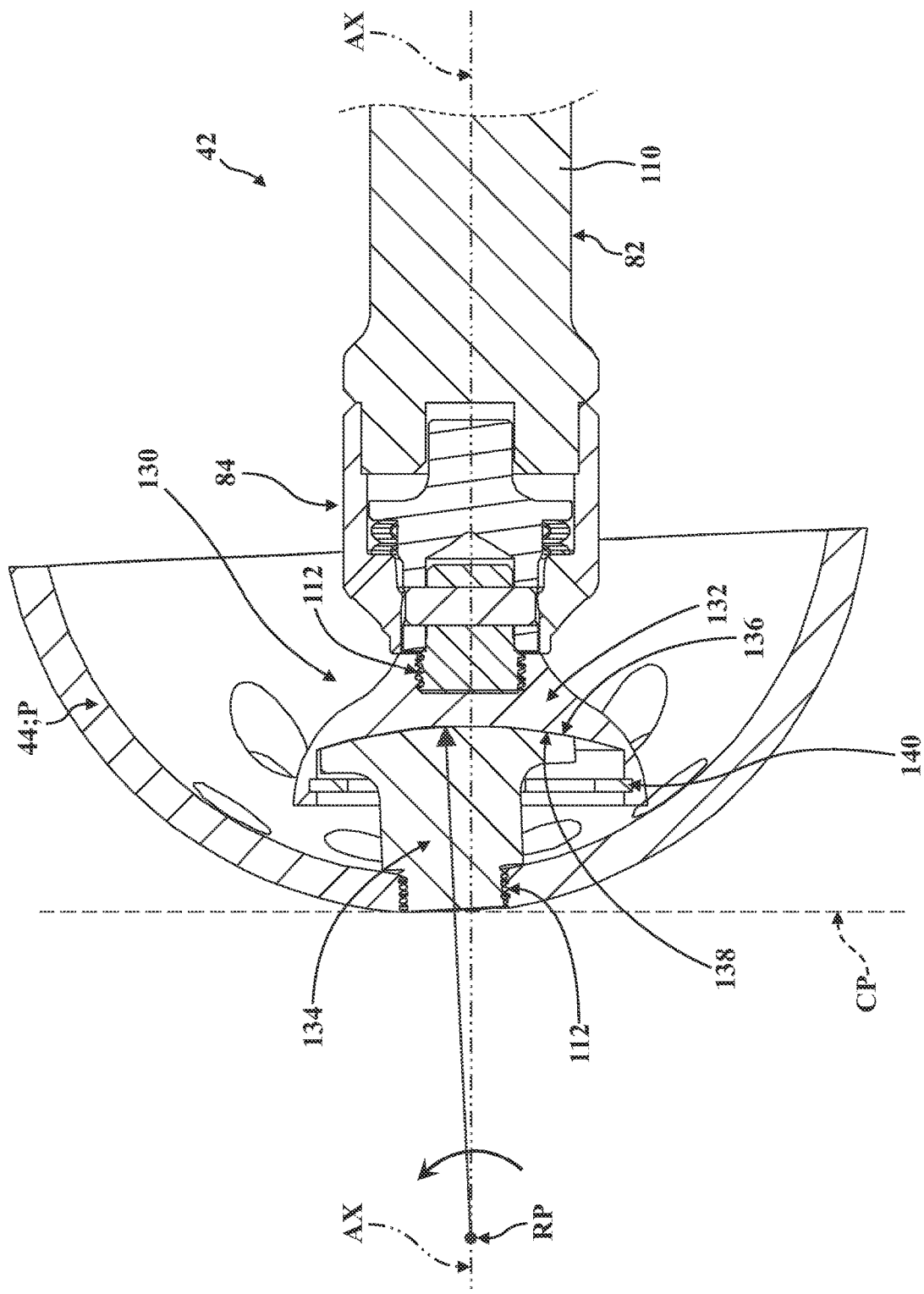
FIG. 19B is another partial section view of the prosthesis, the tool, and the compliance mechanism of FIG. 19A, shown with the prosthesis articulated about the remote point in substantially one direction.
Figure 19C:
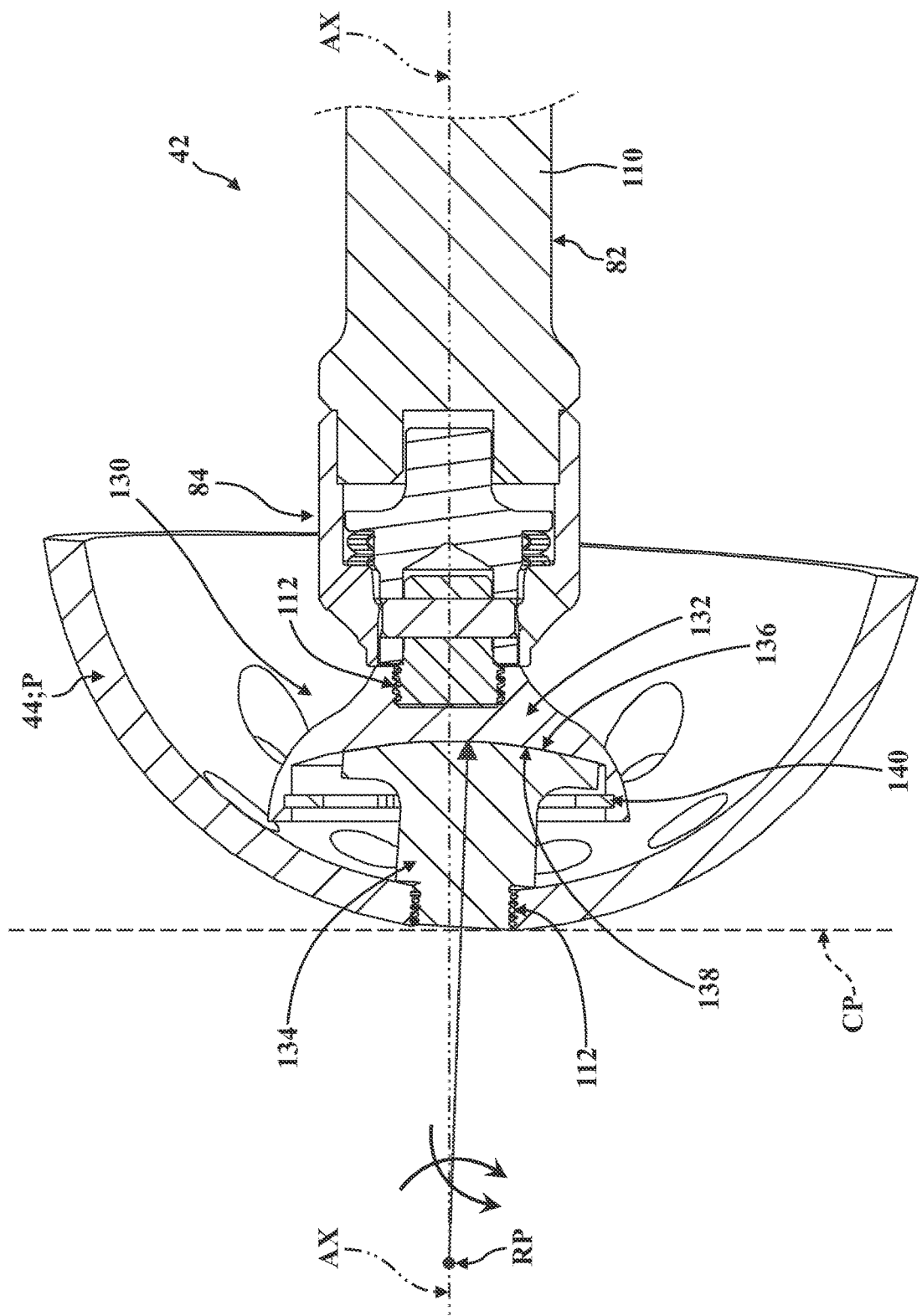
FIG. 19C is another partial section view of the prosthesis, the tool, and the compliance mechanism of FIGS. 19A-19B, shown with the prosthesis articulated about the remote point in multiple directions.

In certain embodiments, and as is depicted in the embodiment illustrated schematically in FIGS. 14A-14C as well as in FIGS. 19A-19C, the compliance mechanism 130 is configured such that the remote point RP is spaced distally from the tool 42 along the axis AX. Thus, the remote point RP is disposed outside of the physical space occupied by the tool 42 and the prosthesis P. This configuration also allows the remote point RP to be disposed below the reamed surface of the acetabulum at the surgical site S, which further promotes the tendency for the application of impact force F to "pull" the prosthesis P toward the remote point RP.

Referring now to FIGS. 16-19C, one embodiment of the compliance mechanism 130 according to the schematic illustration of FIG. 15A is depicted in various orientations. As noted above, the compliance mechanism 130 may be interposed between the prosthesis P and the interface 84 of the second assembly 82, such as by threaded engagement 112. However, it will be appreciated that one or more parts of the compliance mechanism 130 could be formed integrally with the tool 42 without departing from the scope of the present disclosure. By way of non-limiting example, the proximal body 132 could be formed integrally with the second shaft 110.

As is best shown in FIGS. 17-19C, the distal body 134 of the compliance mechanism 130 has a first surface 136 and the proximal body 132 of the compliance mechanism 130 has a second surface 138 shaped to slidably engage the first surface 136 to facilitate movement of the distal body 134 about the remote point RP aligned to the axis AX. To this end, and in the representative embodiment illustrated herein, at least one of the first surface 136 of the distal body 134 and the second surface 138 of the proximal body 132 has a generally spherical profile. In some embodiments, the distal body 134 is arranged for rotation relative to the proximal body 132. It will be appreciated that relative rotation between the distal body 134 and the proximal body 132 can occur in multiple directions about the remote point RP, or relative rotation can be limited to a certain number of directions. In one embodiment, the distal body 134 of the compliance mechanism 130 is arranged for movement within a compliance plane CP defined perpendicularly to the axis AX (see FIGS. 13A-13B and 19A-19C).

In one embodiment, the proximal body 132 of the compliance mechanism 130 is shaped so as to limit movement of the distal body 134 about the remote point RP, such as by restricting angular movement of the distal body 134 to within a predetermined range of angles. Similarly, the proximal body 132 can be sized, shaped, and/or arranged to engage the prosthesis P to limit angular movement of the distal body 134 about the remote point RP.

Figure 18:
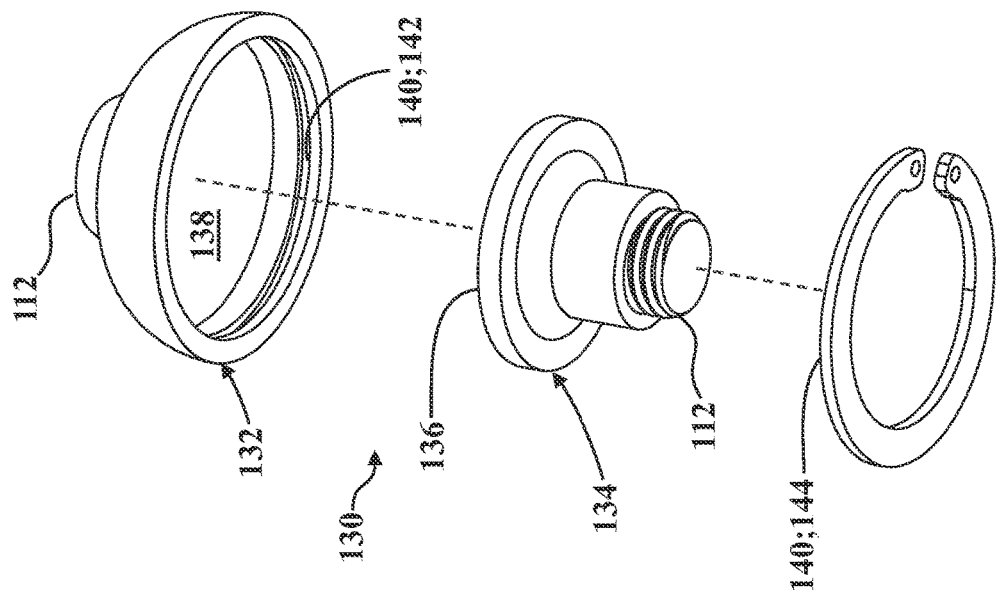
FIG. 18 is another exploded perspective view of the compliance mechanism depicted in FIGS. 16-17.
Figure 17:
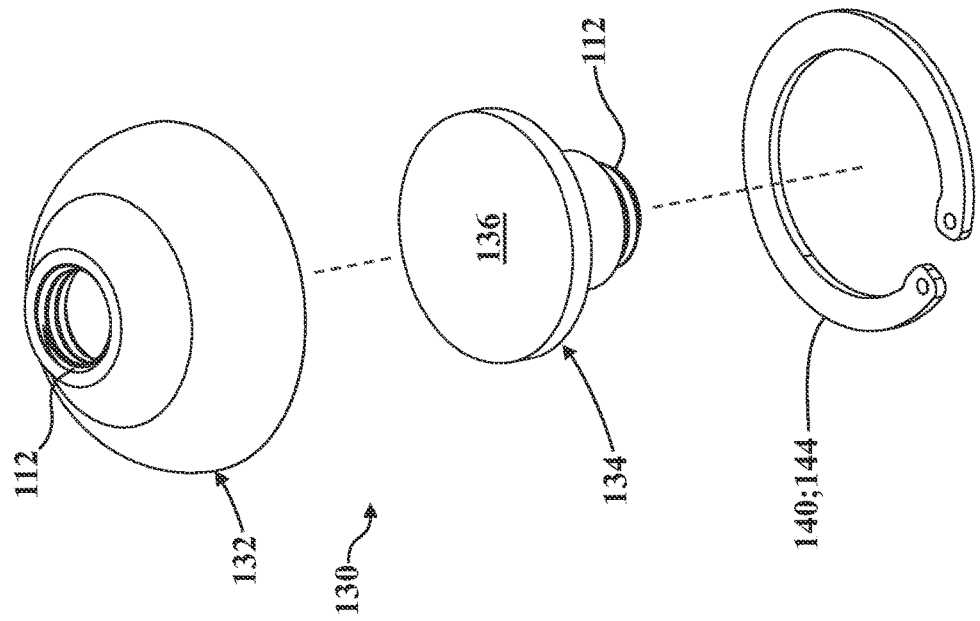
FIG. 17 is an exploded perspective view of the compliance mechanism depicted in FIG. 16.

The proximal body 132 and the distal body 134 of the compliance mechanism 130 are arranged to translate axial force to the distal body 134 that is applied to the proximal body 132 so as to urge the prosthesis P along the axis AX and toward the remote point RP into the surgical site S. As shown in FIGS. 17-18, a retention mechanism 140 may be provided between the proximal body 132 and the distal body 134 to help retain the distal body 134 during use. Here, the proximal body 132 defines a pocket 142 shaped to receive a keeper 144 which, in turn, is shaped to restrict axial movement of the distal body 134 away from the proximal body 132. As shown, the keeper 144 is realized as a circlip, but other arrangements and configurations are contemplated.

FIGS. 19A-19C depict the compliance mechanism 130 and the prosthesis 130 in various orientations. In FIG. 19A, the prosthesis P is aligned to the axis AX in all directions. In FIG. 19B, the prosthesis P and the distal body 134 are articulated about the remote point RP in generally one direction (compare FIG. 19B to FIG. 19A). In FIG. 19C, the prosthesis and the distal body 134 are articulated about the remote point RP in multiple directions (compare FIG. 19C to FIGS. 19A-19B). Here in FIGS. 19A-19C, the remote point RP remains aligned to the axis AX irrespective of the relative position between the proximal body 132 and the distal body 134. Because the remote point RP remains along the axis AX, impact force F applied along the axis AX is likewise aligned with the remote point RP and helps "pull" the prosthesis P toward the remote point RP into alignment with the axis AX during impaction, as noted above.

In this way, the surgical systems 30 and tools 42 described herein afford significant advantages in connection with surgical robots 32 used to carry out a broad number of surgical techniques and procedures. In particular, the alignment and releasable attachment afforded by the coupler 86 and the receiver 88 allow the surgeon to set an impaction trajectory IT and approach the surgical site S and prosthesis P without re-positioning the robotic arm 36 and without requiring significant manipulation of the patient's body B and/or the surgical site S itself. Moreover, while the coupler 86 and the receiver 88 afford significant advantages for procedures involving impaction of prosthetics, those having ordinary skill in the art will appreciate that the coupler 86 and receiver 88 described herein can be used in connection with any suitable type of surgical system 30 tool 42 used to guide any suitable type of workpiece 44 to a desired target 46 with a surgical robot 32.

Furthermore, the compensation for misalignment between the axis AX and the impaction trajectory IT and/or for improperly applied impact force F afforded by the compliance mechanism 130 affords significant advantages in connection with implanting the prosthesis P into the surgical site S. Here too, those having ordinary skill in the art will appreciate that the compliance mechanism 130 is not limited for use with tools 42 adapted for implanting prostheses, and can be used in a broad number of surgical systems 30 to support any suitable type of workpiece 44 guided towards a desired target 46 where the workpiece 44 can move about the remote point RP along the axis AX.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

What is claimed is:

1. A tool for impacting a prosthesis into a surgical site, the tool comprising:
    an impactor head comprising a surface configured to receive an impact force that is manually imparted by a user;
    a tool shaft including a proximal portion and a distal portion, the proximal portion of the tool shaft being fixed to the impactor head; and
    a compliance mechanism comprising:
        a proximal body coupled to the distal portion of the tool shaft and comprising a first surface; and
        a distal body supported by the proximal body and comprising an interface adapted to releasably attach directly to the prosthesis, wherein the distal body is moveable relative to the proximal body for providing compliant motion of the distal body relative to the tool shaft in response to the impact force that is manually imparted by the user, and a second surface shaped to slidably engage the first surface; and
    wherein one of the first surface or the second surface is convex and the other one of the first surface or the second surface is concave.

2. The tool of claim 1, wherein, when the distal body is attached to the prosthesis, the distal body and the prosthesis are concurrently moveable relative to the proximal body, and the distal body provides compliant motion for the prosthesis relative to the tool shaft to guide the prosthesis into alignment with the surgical site in response to the impact force that is manually imparted by the user.

3. The tool of claim 1, wherein:
    the tool shaft comprises an axis;
    the proximal body is fixed relative to the axis of the tool shaft; and
    the proximal body is configured to support movement of the distal body about a remote center of motion.

4. The tool of claim 1, wherein the proximal body defines a pocket and the first surface of the proximal body is located within the pocket, wherein the second surface of the distal body is configured to interface with the first surface within the pocket, and wherein a retention mechanism is coupled to the pocket for compliantly retaining the distal body to the proximal body.

5. The tool of claim 1, wherein the distal body is configured to rotate relative to the proximal body.

6. The tool of claim 1, wherein the interface of the distal body is threaded to couple to a corresponding threaded interface of the prosthesis.

7. An assembly comprising:
    a prosthesis; and
    a tool comprising:
        an impactor head comprising a surface configured to receive an impact force that is manually imparted by a user;
        a tool shaft including a proximal portion and a distal portion, the proximal portion of the tool shaft being fixed to the impactor head; and
        a compliance mechanism comprising:
            a proximal body coupled to the distal portion of the tool shaft; and
            a distal body supported by the proximal body and comprising an interface attaching directly to the prosthesis, the distal body and the prosthesis are concurrently moveable relative to the proximal body, and the distal body provides compliant motion for the prosthesis relative to the tool shaft in response to the impact force that is manually imparted by the user; and
    wherein the prosthesis comprises:
        a hip implant including a cavity; and
        a threaded interface;
    wherein the proximal body and the distal body of the compliance mechanism are disposed within the cavity of the prosthesis; and
    wherein the interface of the distal body is threaded to couple to the threaded interface of the prosthesis.

8. The assembly of claim 7, wherein:
    the tool shaft comprises an axis;
    the proximal body is fixed relative to the axis of the tool shaft; and
    the proximal body is configured to support movement of the distal body about a remote center of motion.

9. The assembly of claim 7, wherein:
    the proximal body comprises a first surface; and
    the distal body comprises a second surface shaped to slidably engage the first surface.

10. The assembly of claim 9, wherein one of the first surface or the second surface is convex and the other one of the first surface or the second surface is concave.

11. The assembly of claim 9, wherein the proximal body defines a pocket and the first surface of the proximal body is located within the pocket, wherein the second surface of the distal body is configured to interface with the first surface within the pocket, and wherein a retention mechanism is coupled to the pocket for compliantly retaining the distal body to the proximal body.

12. The assembly of claim 7, wherein the distal body is configured to rotate relative to the proximal body.

13. A surgical system comprising:
   a surgical robot comprising a base, an arm coupled to the base, and a tool guide coupled to the arm; and
   a tool for impacting a prosthesis into a surgical site, the tool comprising:
      an impactor head comprising a surface configured to receive an impact force that is manually imparted by a user;
      a tool shaft configured to be supported by the tool guide for alignment of the tool shaft relative to the surgical site, the tool shaft including a proximal portion and a distal portion, the proximal portion of the tool shaft being fixed to the impactor head; and
      a compliance mechanism comprising:
         a proximal body coupled to the distal portion of the tool shaft and comprising a first surface; and
         a distal body supported by the proximal body and comprising an interface adapted to releasably attach directly to the prosthesis, wherein the distal body is moveable relative to the proximal body for providing compliant motion of the distal body relative to the tool shaft in response to the impact force that is manually imparted by the user, and a second surface shaped to slidably engage the first surface; and
      wherein one of the first surface or the second surface is convex and the other one of the first surface or the second surface is concave.

14. The surgical system of claim 13, wherein:
   the tool shaft comprises an axis;
   the proximal body is fixed relative to the axis of the tool shaft;
   the proximal body is configured to support movement of the distal body about a remote center of motion;
   the proximal body comprises a first surface; and
   the distal body comprises a second surface shaped to slidably engage the first surface.

* * * * *